United States Patent
Osborne et al.

(10) Patent No.: US 11,324,911 B2
(45) Date of Patent: May 10, 2022

(54) FLOW MIXERS FOR RESPIRATORY THERAPY SYSTEMS

(71) Applicant: Fisher & Paykel Healthcare Limited, Auckland (NZ)

(72) Inventors: Hamish Adrian Osborne, Auckland (NZ); Niall Christopher Denham, Auckland (NZ); Mahran Maumoon Sujau, Auckland (NZ); Andre Van Schalkwyk, Auckland (NZ); Ivan Justus Rademeyer, Auckland (NZ); Tessa Hazel Paris, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 420 days.

(21) Appl. No.: 15/315,669

(22) PCT Filed: Jun. 3, 2015

(86) PCT No.: PCT/NZ2015/050069
§ 371 (c)(1),
(2) Date: Dec. 1, 2016

(87) PCT Pub. No.: WO2015/187039
PCT Pub. Date: Dec. 10, 2015

(65) Prior Publication Data
US 2017/0197057 A1 Jul. 13, 2017

Related U.S. Application Data

(60) Provisional application No. 62/007,095, filed on Jun. 3, 2014.

(51) Int. Cl.
*A61M 16/12* (2006.01)
*A61M 16/16* (2006.01)
(Continued)

(52) U.S. Cl.
CPC ........ *A61M 16/12* (2013.01); *A61M 16/0003* (2014.02); *A61M 16/0066* (2013.01);
(Continued)

(58) Field of Classification Search
CPC .............. A61M 16/00; A61M 16/0003; A61M 16/0057; A61M 16/0066; A61M 16/0069;
(Continued)

(56) References Cited

U.S. PATENT DOCUMENTS

| 1,085,833 | A | 2/1914 | Wilson |
| 1,154,259 | A | 9/1915 | Light |

(Continued)

FOREIGN PATENT DOCUMENTS

| AU | 667538 | 3/1996 |
| AU | 726022 | 10/2000 |

(Continued)

OTHER PUBLICATIONS

Sep. 4, 2015, International Search Report for PCT/NZ2015/050069 filed on Jun. 3, 2015.

(Continued)

*Primary Examiner* — Justine R Yu
*Assistant Examiner* — Matthew D Ziegler
(74) *Attorney, Agent, or Firm* — Knobbe Martens Olson & Bear, LLP

(57) ABSTRACT

A flow of gases in a respiratory therapy system can be conditioned to achieve more consistent output from sensors configured to sense a characteristic of the flow. The flow can be mixed by imparting a tangential, rotary, helical, or swirling motion to the flow of gases. The mixing can occur upstream of the sensors. The flow can be segregated into smaller compartments to reduce turbulence in a region of the sensors.

28 Claims, 26 Drawing Sheets

(51) Int. Cl.
*A61M 16/10* (2006.01)
*A61M 16/08* (2006.01)
*A61M 16/00* (2006.01)

(52) U.S. Cl.
CPC ...... *A61M 16/024* (2017.08); *A61M 16/0816* (2013.01); *A61M 16/109* (2014.02); *A61M 16/122* (2014.02); *A61M 16/16* (2013.01); *A61M 16/0069* (2014.02); *A61M 16/161* (2014.02); *A61M 2016/003* (2013.01); *A61M 2016/0039* (2013.01); *A61M 2016/103* (2013.01); *A61M 2016/1025* (2013.01); *A61M 2205/3368* (2013.01); *A61M 2205/505* (2013.01); *A61M 2206/11* (2013.01); *A61M 2206/14* (2013.01); *A61M 2206/16* (2013.01); *A61M 2230/06* (2013.01); *A61M 2230/10* (2013.01); *A61M 2230/201* (2013.01); *A61M 2230/202* (2013.01); *A61M 2230/205* (2013.01)

(58) Field of Classification Search
CPC ................ A61M 16/024; A61M 16/08; A61M 16/0816; A61M 16/10; A61M 16/109; A61M 16/12; A61M 16/122; A61M 16/16–168; A61M 2016/003; A61M 2016/0039; A61M 2016/1025; A61M 2016/103; A61M 2205/07; A61M 2205/33; A61M 2205/3331; A61M 2205/3368; A61M 2205/50; A61M 2205/502; A61M 2205/505; A61M 2206/11; A61M 2206/14; A61M 2206/16; A61M 2230/06; A61M 2230/10; A61M 2230/20; A61M 2230/201; A61M 2230/202; A61M 2230/205; A61M 2202/0007; A61M 2202/02; A61M 2202/0208; A61M 2210/06; A61M 2210/0625; A61M 16/0051; A61M 16/0841–0858; A61M 16/0875–0883; A61M 16/14; A61M 2016/0033; A61M 2016/0027; F28F 9/22; F28F 2009/222; F28F 2009/224; F28F 2009/228

See application file for complete search history.

(56) References Cited

U.S. PATENT DOCUMENTS

| | | | |
|---|---|---|---|
| 2,073,335 A | 3/1937 | Connell | |
| 2,510,125 A | 6/1950 | Meakin | |
| 2,516,864 A | 8/1950 | Gilmore et al. | |
| 2,745,074 A | 1/1951 | Darling | |
| 2,590,797 A | 3/1952 | Siciliano | |
| 2,621,875 A | 12/1952 | Darling | |
| 2,634,311 A | 4/1953 | Darling | |
| 3,117,596 A | 1/1964 | Kahn | |
| 3,163,707 A | 12/1964 | Darling | |
| 3,283,580 A | 11/1966 | Jacob et al. | |
| 3,394,954 A | 7/1968 | Sarns | |
| 3,404,684 A | 10/1968 | Brewer et al. | |
| 3,485,237 A | 12/1969 | Bedford | |
| 3,495,628 A | 2/1970 | Boender | |
| 3,582,094 A | 6/1971 | Whittaker | |
| 3,588,859 A | 6/1971 | Petree | |
| 3,623,511 A | 11/1971 | Levin | |
| 3,638,926 A | 2/1972 | Melville et al. | |
| 3,659,604 A | 5/1972 | Melville et al. | |
| 3,703,892 A | 11/1972 | Meyers | |
| 3,777,298 A | 12/1973 | Newman | |
| 3,806,102 A | 4/1974 | Valenta et al. | |
| 3,903,742 A | 9/1975 | Colton | |
| 3,945,378 A | 3/1976 | Paluch | |
| 3,954,920 A | 5/1976 | Heath | |
| 3,987,133 A | 10/1976 | Andra | |
| 3,990,727 A | 11/1976 | Gallagher | |
| 4,010,748 A | 3/1977 | Dobritz | |
| 4,028,444 A | 6/1977 | Brown | |
| 4,038,519 A | 7/1977 | Foucras | |
| 4,060,576 A | 11/1977 | Grant | |
| 4,098,853 A | 7/1978 | Brown et al. | |
| 4,111,197 A | 9/1978 | Warncke et al. | |
| 4,139,762 A | 2/1979 | Pohrer et al. | |
| 4,152,379 A | 5/1979 | Suhr | |
| 4,160,466 A | 7/1979 | Jousson | |
| 4,172,709 A | 10/1979 | Kippel et al. | |
| 4,183,248 A | 1/1980 | West | |
| 4,192,836 A * | 3/1980 | Bartscher | A61M 16/167 128/200.11 |
| 4,301,200 A | 11/1981 | Langenfeld et al. | |
| 4,333,451 A | 6/1982 | Paluch | |
| 4,417,574 A | 11/1983 | Taloon et al. | |
| 4,428,403 A | 1/1984 | Lee | |
| 4,463,593 A | 8/1984 | Parker | |
| 4,473,923 A | 10/1984 | Neroni et al. | |
| 4,529,867 A | 7/1985 | Velnosky et al. | |
| 4,531,551 A | 7/1985 | Eichelberger et al. | |
| 4,533,115 A | 8/1985 | Lissau | |
| 4,545,290 A | 10/1985 | Lieberman | |
| 4,558,708 A | 12/1985 | Labuda et al. | |
| 4,564,748 A | 1/1986 | Gupton | |
| 4,588,425 A | 5/1986 | Usry et al. | |
| 4,599,895 A * | 7/1986 | Wiseman | G01F 1/696 73/204.18 |
| 4,621,632 A | 11/1986 | Bartels et al. | |
| 4,676,237 A | 6/1987 | Wood et al. | |
| 4,686,354 A | 8/1987 | Makin | |
| 4,708,831 A | 11/1987 | Elsworth et al. | |
| 4,714,078 A | 12/1987 | Paluch | |
| 4,753,758 A | 6/1988 | Miller | |
| 4,774,032 A | 9/1988 | Coates et al. | |
| 4,809,698 A | 3/1989 | Kogo | |
| 4,813,280 A | 3/1989 | Miller, Jr. et al. | |
| 4,830,515 A | 5/1989 | Cortes | |
| 4,844,512 A | 7/1989 | Gahwiler | |
| 4,942,877 A | 7/1990 | Sakai et al. | |
| 4,944,310 A | 7/1990 | Sullivan | |
| 4,967,744 A | 11/1990 | Chua | |
| 5,017,875 A | 5/1991 | Hori | |
| 5,027,811 A | 7/1991 | Tuxill | |
| 5,031,612 A | 7/1991 | Clementi | |
| 5,038,773 A * | 8/1991 | Norlien | A61B 5/087 128/205.23 |
| 5,054,819 A | 10/1991 | Grunwald | |
| 5,058,588 A | 10/1991 | Kaestle | |
| 5,060,506 A | 10/1991 | Douglas | |
| 5,062,145 A * | 10/1991 | Zwaan | A61M 16/16 392/395 |
| 5,117,819 A | 6/1992 | Servidio et al. | |
| 5,127,442 A | 7/1992 | Blomqvist | |
| 5,134,996 A | 8/1992 | Bell | |
| 5,143,060 A | 9/1992 | Smith | |
| 5,148,801 A | 9/1992 | Douwens et al. | |
| 5,181,858 A | 1/1993 | Matz et al. | |
| 5,209,225 A | 5/1993 | Glenn | |
| 5,213,138 A | 5/1993 | Presz, Jr. | |
| 5,213,376 A | 5/1993 | Szabo | |
| 5,233,996 A | 8/1993 | Coleman et al. | |
| 5,303,701 A | 4/1994 | Heins et al. | |
| RE34,599 E | 5/1994 | Suszynski et al. | |
| 5,342,126 A | 8/1994 | Heston | |
| 5,357,948 A | 10/1994 | Eilentropp | |
| 5,367,604 A * | 11/1994 | Murray | A61M 16/1075 392/394 |
| 5,392,770 A | 2/1995 | Clawson et al. | |
| 5,396,884 A | 3/1995 | Bagwell et al. | |
| 5,454,061 A | 9/1995 | Carlson | |
| 5,454,479 A | 10/1995 | Kraus | |
| 5,483,616 A | 1/1996 | Chiu et al. | |
| 5,484,223 A | 1/1996 | Saito | |
| 5,488,447 A | 1/1996 | Patton | |
| 5,495,872 A | 3/1996 | Gallagher et al. | |

(56) References Cited

U.S. PATENT DOCUMENTS

| | | | |
|---|---|---|---|
| 5,499,737 A | 3/1996 | Kraus | |
| RE35,225 E | 4/1996 | Herweck et al. | |
| 5,529,093 A | 6/1996 | Gallagher et al. | |
| 5,537,996 A | 7/1996 | McPhee | |
| 5,540,219 A | 7/1996 | Mechlenburg et al. | |
| 5,548,879 A | 8/1996 | Wu | |
| 5,551,883 A | 9/1996 | Davis | |
| 5,558,084 A | 9/1996 | Daniell | |
| 5,564,415 A | 10/1996 | Dobson et al. | |
| 5,598,837 A | 2/1997 | Sirianne et al. | |
| 5,600,752 A | 2/1997 | Lopatinsky | |
| 5,630,806 A | 5/1997 | Inagaki et al. | |
| 5,637,006 A | 6/1997 | Almeras | |
| 5,640,951 A | 6/1997 | Huddart et al. | |
| 5,660,567 A | 8/1997 | Nierlich et al. | |
| 5,667,306 A | 9/1997 | Montreuil | |
| 5,720,293 A | 2/1998 | Nierlich et al. | |
| 5,778,872 A | 7/1998 | Fukunaga et al. | |
| 5,829,880 A | 11/1998 | Diedrich | |
| 5,881,393 A | 3/1999 | Marchello | |
| 5,906,201 A | 5/1999 | Nilson | |
| 5,913,249 A * | 6/1999 | Weckstrom | A61B 5/087 73/861.52 |
| 5,943,473 A | 8/1999 | Levine | |
| 5,975,591 A | 11/1999 | Guest | |
| 5,979,247 A * | 11/1999 | Kizawa | G01F 1/42 73/861.53 |
| D419,522 S | 1/2000 | Kamagai | |
| 6,024,694 A * | 2/2000 | Goldberg | A61G 11/00 600/22 |
| 6,039,696 A | 3/2000 | Bell | |
| 6,050,260 A * | 4/2000 | Daniell | A61M 16/1075 128/203.12 |
| 6,053,482 A | 4/2000 | Glenn et al. | |
| 6,058,977 A | 5/2000 | Hotta | |
| 6,078,729 A | 6/2000 | Kopel | |
| 6,078,730 A | 6/2000 | Huddart et al. | |
| 6,095,505 A * | 8/2000 | Miller | A61M 16/1075 128/203.27 |
| 6,102,037 A | 8/2000 | Koch | |
| 6,105,970 A | 8/2000 | Siegrist et al. | |
| 6,126,610 A | 10/2000 | Rich et al. | |
| 6,128,963 A * | 10/2000 | Bromster | G01F 1/36 73/861.52 |
| 6,138,674 A | 10/2000 | Gull et al. | |
| 6,190,480 B1 | 2/2001 | Carlson | |
| 6,196,980 B1 | 3/2001 | Akerfeldt et al. | |
| 6,201,983 B1 | 3/2001 | Haumann et al. | |
| 6,208,514 B1 | 3/2001 | Stark | |
| 6,226,451 B1 | 5/2001 | Wong | |
| 6,272,933 B1 * | 8/2001 | Gradon | A61M 16/1075 128/203.16 |
| 6,332,462 B1 | 12/2001 | Krohn | |
| 6,347,646 B2 | 2/2002 | Fikui | |
| 6,349,722 B1 | 2/2002 | Gradon et al. | |
| 6,349,724 B1 | 2/2002 | Burton et al. | |
| 6,360,741 B2 | 3/2002 | Truschel | |
| 6,367,974 B1 | 4/2002 | Lin | |
| 6,374,864 B1 | 4/2002 | Philip | |
| 6,394,145 B1 | 5/2002 | Gessil | |
| 6,397,841 B1 | 6/2002 | Kenyon et al. | |
| 6,402,207 B1 | 6/2002 | Segal et al. | |
| 6,435,180 B1 | 8/2002 | Hewson et al. | |
| 6,467,477 B1 | 10/2002 | Frank et al. | |
| 6,508,249 B2 | 1/2003 | Hoenig | |
| 6,511,075 B1 | 1/2003 | Schmidt | |
| 6,540,734 B1 | 4/2003 | Chiu | |
| 6,551,143 B2 | 4/2003 | Tanaka et al. | |
| 6,554,260 B1 | 4/2003 | Lipscombe et al. | |
| 6,591,061 B2 | 7/2003 | Wang | |
| 6,598,604 B1 | 7/2003 | Seakins | |
| 6,600,727 B1 | 7/2003 | Mackay | |
| 6,612,624 B1 | 9/2003 | Segal et al. | |
| 6,623,352 B2 | 9/2003 | Illingworth | |
| 6,631,718 B1 | 10/2003 | Lovell | |
| 6,648,669 B1 | 11/2003 | Kim et al. | |
| 6,655,207 B1 * | 12/2003 | Speldrich | G01F 1/40 73/202.5 |
| 6,668,828 B1 | 12/2003 | Figley et al. | |
| 6,685,491 B2 | 2/2004 | Gergek | |
| 6,698,966 B2 | 3/2004 | Hilton et al. | |
| 6,824,180 B2 | 11/2004 | Tomchak | |
| 6,827,084 B2 | 12/2004 | Grubb, Jr. | |
| 6,874,771 B2 | 4/2005 | Birdsell et al. | |
| 6,895,803 B2 | 5/2005 | Seakins et al. | |
| 6,915,705 B1 * | 7/2005 | Truitt | A61B 5/087 73/861.52 |
| 6,918,389 B2 | 7/2005 | Seakiins et al. | |
| 6,935,337 B2 | 8/2005 | Virr et al. | |
| 6,943,566 B2 | 9/2005 | Florin et al. | |
| 6,953,354 B2 | 10/2005 | Edirisuriya et al. | |
| 7,043,979 B2 | 5/2006 | Smith et al. | |
| 7,063,668 B2 | 6/2006 | Cardelius et al. | |
| 7,086,422 B2 | 8/2006 | Huber et al. | |
| 7,090,541 B2 | 8/2006 | Ho | |
| 7,096,864 B1 | 8/2006 | Mayer et al. | |
| 7,120,354 B2 | 10/2006 | Mackie et al. | |
| 7,137,654 B2 | 11/2006 | Segal et al. | |
| 7,140,367 B2 | 11/2006 | White et al. | |
| 7,157,035 B2 | 1/2007 | Edirisuriya et al. | |
| 7,191,780 B2 | 3/2007 | Faram | |
| 7,225,809 B1 | 6/2007 | Bowen et al. | |
| 7,284,554 B2 | 10/2007 | Shaw | |
| 7,316,768 B2 | 1/2008 | Aldridge et al. | |
| 7,316,769 B2 | 1/2008 | Aldridge | |
| 7,327,547 B1 | 2/2008 | Epstein | |
| 7,327,949 B1 | 2/2008 | Cheng et al. | |
| 7,334,587 B2 | 2/2008 | Lake | |
| 7,364,436 B2 | 4/2008 | Yen | |
| 7,396,995 B2 | 7/2008 | Laurent et al. | |
| 7,448,383 B2 | 11/2008 | Delache et al. | |
| 7,469,586 B2 | 12/2008 | Wild et al. | |
| 7,478,635 B2 | 1/2009 | Wixey et al. | |
| 7,525,663 B2 | 4/2009 | Kwok et al. | |
| 7,607,360 B2 * | 10/2009 | Todokoro | G01F 1/46 73/861.61 |
| 7,614,398 B2 | 11/2009 | Virr et al. | |
| 7,637,288 B2 | 12/2009 | Kressierer/Huber et al. | |
| 7,677,246 B2 | 3/2010 | Kepler et al. | |
| 7,743,767 B2 | 6/2010 | Ging et al. | |
| 7,766,050 B2 | 8/2010 | Patel | |
| 7,794,426 B2 | 9/2010 | Briones et al. | |
| 7,814,907 B2 | 10/2010 | Bremner et al. | |
| 7,816,888 B2 | 10/2010 | Rejman et al. | |
| D628,288 S | 11/2010 | Row et al. | |
| 7,827,981 B2 | 11/2010 | Barnford | |
| 7,870,857 B2 | 1/2011 | Dhuper et al. | |
| 7,874,291 B2 | 1/2011 | Ging et al. | |
| 7,900,528 B2 | 3/2011 | Vincent | |
| 7,913,689 B2 | 3/2011 | Henry et al. | |
| 7,942,380 B2 | 5/2011 | Bertinetti et al. | |
| 7,942,389 B2 | 5/2011 | Koch et al. | |
| 7,965,930 B2 | 6/2011 | Carlson et al. | |
| 7,983,542 B2 | 7/2011 | McGhin et al. | |
| 7,987,847 B2 | 8/2011 | Wickham | |
| 7,992,554 B2 | 8/2011 | Radomski et al. | |
| 7,997,267 B2 | 8/2011 | Ging et al. | |
| 8,025,849 B2 | 9/2011 | Baldwin et al. | |
| 8,059,947 B2 | 11/2011 | Bradley et al. | |
| 8,063,343 B2 | 11/2011 | McGhin et al. | |
| 8,078,040 B2 | 12/2011 | Forrester | |
| 8,100,124 B2 | 1/2012 | Becker et al. | |
| 8,122,882 B2 | 2/2012 | McGhin et al. | |
| 8,136,521 B2 | 3/2012 | Matthews et al. | |
| 8,137,082 B2 | 3/2012 | Campbell | |
| 8,181,940 B2 | 5/2012 | Payne et al. | |
| 8,182,144 B2 | 5/2012 | Koch | |
| 8,186,345 B2 | 5/2012 | Payton et al. | |
| 8,186,352 B2 | 5/2012 | Gunaratnam et al. | |
| 8,197,123 B2 | 6/2012 | Snyder et al. | |
| 8,206,337 B2 * | 6/2012 | Blackhurst | A61B 1/00154 604/26 |
| 8,221,530 B2 | 7/2012 | Peter et al. | |

(56) References Cited

U.S. PATENT DOCUMENTS

| | | | |
|---|---|---|---|
| 8,226,293 B2 | 7/2012 | Faries, Jr. | |
| 8,240,306 B2 | 8/2012 | Cortez, Jr. et al. | |
| 8,245,709 B2 | 8/2012 | Rossen et al. | |
| 8,245,710 B2 | 8/2012 | Makinson et al. | |
| 8,253,076 B2 | 8/2012 | Andel et al. | |
| 8,267,084 B2 | 8/2012 | Kwok | |
| 8,257,286 B2 | 9/2012 | Meyer et al. | |
| 8,267,614 B2 | 9/2012 | Khoe | |
| 8,282,427 B2 | 10/2012 | Yamazaki | |
| 8,287,517 B2 | 10/2012 | Hanlon et al. | |
| 8,316,848 B2 | 11/2012 | Kwok et al. | |
| 8,333,194 B2 | 12/2012 | Hanlon et al. | |
| 8,333,195 B2 | 12/2012 | Cortez, Jr. et al. | |
| 8,333,199 B2 | 12/2012 | Landis et al. | |
| 8,355,753 B2 | 1/2013 | Bochensko et al. | |
| 8,360,059 B2 | 1/2013 | Koulechov et al. | |
| 8,365,726 B2 | 2/2013 | Snow et al. | |
| 8,381,724 B2 | 2/2013 | Bowen et al. | |
| 8,424,514 B2 | 4/2013 | Oates et al. | |
| 8,453,641 B2 | 6/2013 | Payton et al. | |
| 8,453,643 B2 | 6/2013 | Sanchez et al. | |
| 8,459,261 B2 * | 6/2013 | Ricciardelli | A61B 5/091 128/204.23 |
| 8,469,025 B2 | 6/2013 | Mayer et al. | |
| 8,490,621 B2 | 7/2013 | Radomski et al. | |
| 8,496,001 B2 | 7/2013 | Schermeier et al. | |
| RE44,453 E | 8/2013 | Virr et al. | |
| 8,511,305 B2 | 8/2013 | Liu et al. | |
| 8,511,651 B2 | 8/2013 | Fridberg et al. | |
| 8,516,911 B2 | 8/2013 | Inoue | |
| 8,522,782 B2 | 9/2013 | Lewis et al. | |
| 8,528,552 B2 | 9/2013 | von Blumenthal | |
| 8,544,465 B2 | 10/2013 | Smith et al. | |
| 8,545,096 B2 | 10/2013 | Reiter | |
| 8,550,072 B2 | 10/2013 | Thudor et al. | |
| 8,631,789 B2 | 1/2014 | Virr et al. | |
| 8,640,560 B2 | 2/2014 | Burke | |
| 8,640,696 B2 | 2/2014 | Pujol et al. | |
| 8,651,800 B2 | 2/2014 | Li | |
| 8,733,348 B2 | 5/2014 | Korneff et al. | |
| 8,733,349 B2 | 5/2014 | Bath et al. | |
| 8,756,990 B2 * | 6/2014 | Speldrich | B29C 45/0025 73/273 |
| 8,776,790 B2 * | 7/2014 | Gentner | A61M 16/00 128/204.18 |
| 8,783,252 B2 | 7/2014 | Pierro et al. | |
| 8,800,970 B2 | 8/2014 | Heine et al. | |
| 8,770,190 B2 | 9/2014 | McCarthy | |
| 8,844,388 B2 | 9/2014 | Burke | |
| 8,844,521 B2 | 9/2014 | McCarthy | |
| 8,851,071 B2 | 10/2014 | Kuo et al. | |
| 8,905,023 B2 | 12/2014 | Niland et al. | |
| 8,915,250 B2 | 12/2014 | Dugan et al. | |
| 8,931,481 B2 | 1/2015 | Jones et al. | |
| 8,939,147 B2 | 1/2015 | Henry et al. | |
| 8,985,105 B2 | 3/2015 | Burton et al. | |
| 9,022,946 B2 | 5/2015 | Haque | |
| 9,039,277 B2 | 5/2015 | Le Bouquin et al. | |
| 9,067,036 B2 | 6/2015 | Kornell et al. | |
| 9,095,668 B2 | 8/2015 | Blackhurst et al. | |
| 9,119,933 B2 | 9/2015 | Bedford et al. | |
| 9,132,252 B2 | 9/2015 | Barlow et al. | |
| 9,162,035 B2 | 10/2015 | Kwok | |
| 9,186,477 B2 | 11/2015 | Hunt et al. | |
| 9,205,220 B2 | 12/2015 | Korneff et al. | |
| 9,212,673 B2 | 12/2015 | Korneff et al. | |
| 9,242,064 B2 | 1/2016 | Rustad et al. | |
| 9,254,368 B2 | 2/2016 | Blumental et al. | |
| 9,289,572 B2 | 3/2016 | Korneff et al. | |
| RE46,079 E | 7/2016 | Virr et al. | |
| 9,381,317 B2 | 7/2016 | Landis et al. | |
| 9,387,299 B2 | 7/2016 | Zwolinsky et al. | |
| 9,427,547 B2 | 8/2016 | Landis et al. | |
| 9,446,210 B2 | 9/2016 | Orr et al. | |
| 9,512,856 B2 * | 12/2016 | Nibu | A61M 16/0066 |
| 9,517,321 B2 | 12/2016 | Buechi et al. | |
| 9,545,493 B2 | 1/2017 | Mayer et al. | |
| 9,566,409 B2 | 2/2017 | Gründler et al. | |
| 9,572,949 B2 | 2/2017 | Vos et al. | |
| 9,572,951 B2 | 2/2017 | Barker et al. | |
| 9,586,019 B2 | 3/2017 | Heine et al. | |
| 9,642,979 B2 | 5/2017 | Korneff et al. | |
| RE46,571 E | 10/2017 | Virr et al. | |
| 9,838,759 B2 | 12/2017 | Kirmse et al. | |
| 9,861,778 B2 | 1/2018 | Roderick et al. | |
| 9,937,314 B2 | 4/2018 | Buechi et al. | |
| 9,937,316 B2 | 4/2018 | Buechi et al. | |
| 9,974,921 B2 | 5/2018 | Klenner et al. | |
| 9,987,455 B2 | 6/2018 | Stoks et al. | |
| 10,046,136 B2 | 8/2018 | Pujol | |
| 10,245,407 B2 | 4/2019 | Osborne et al. | |
| 10,449,319 B2 | 10/2019 | Osborne et al. | |
| 10,828,482 B2 | 11/2020 | Osborne et al. | |
| 10,974,015 B2 | 4/2021 | Stoks et al. | |
| 11,129,956 B2 | 9/2021 | Klenner et al. | |
| 2001/0017134 A1 | 8/2001 | Bahr | |
| 2001/0017880 A1 | 8/2001 | Beerwerth et al. | |
| 2001/0050080 A1 | 12/2001 | Seakins et al. | |
| 2002/0058436 A1 | 5/2002 | Saba | |
| 2002/0100320 A1 | 8/2002 | Smith et al. | |
| 2002/0132511 A1 | 9/2002 | Groebe et al. | |
| 2002/0153011 A1 * | 10/2002 | Tanhehco | A61M 16/20 128/204.18 |
| 2003/0066526 A1 | 4/2003 | Thurdor et al. | |
| 2003/0066530 A1 | 4/2003 | Shahbazpour et al. | |
| 2003/0107325 A1 | 6/2003 | Birkhead | |
| 2003/0127096 A1 * | 7/2003 | McAuliffe | A61M 16/20 128/204.18 |
| 2003/0148664 A1 | 8/2003 | Cheng | |
| 2003/0154977 A1 | 8/2003 | White et al. | |
| 2003/0183294 A1 | 10/2003 | Carlson | |
| 2003/0200727 A1 | 10/2003 | Kim | |
| 2003/0236015 A1 | 12/2003 | Edirisuriya et al. | |
| 2004/0013162 A1 | 1/2004 | Beerwerth et al. | |
| 2004/0055597 A1 | 3/2004 | Virr et al. | |
| 2004/0074493 A1 | 4/2004 | Seakins et al. | |
| 2004/0079371 A1 | 4/2004 | Gray | |
| 2004/0087213 A1 | 5/2004 | Kao | |
| 2004/0099268 A1 | 5/2004 | Smith et al. | |
| 2004/0101026 A1 | 5/2004 | Nitta et al. | |
| 2004/0149284 A1 | 8/2004 | Smith et al. | |
| 2004/0168530 A1 | 9/2004 | Adolfs | |
| 2004/0182392 A1 | 9/2004 | Gerder et al. | |
| 2004/0221843 A1 | 11/2004 | Baecke | |
| 2004/0234254 A1 | 11/2004 | Czupich et al. | |
| 2004/0239001 A1 | 12/2004 | Edirisuriya et al. | |
| 2004/0244858 A1 | 12/2004 | Jeong | |
| 2005/0039809 A1 | 2/2005 | Speldrich | |
| 2005/0059957 A1 | 3/2005 | Campbell et al. | |
| 2005/0152733 A1 | 7/2005 | Patel | |
| 2006/0030191 A1 | 2/2006 | Tuin et al. | |
| 2006/0118113 A1 | 6/2006 | Bremner et al. | |
| 2006/0137445 A1 | 6/2006 | Smith et al. | |
| 2006/0150712 A1 * | 7/2006 | Berstis | A61M 16/10 73/23.2 |
| 2006/0165829 A1 | 7/2006 | Smith et al. | |
| 2006/0196510 A1 | 9/2006 | McDonald | |
| 2006/0237012 A1 | 10/2006 | Thurdor et al. | |
| 2006/0249160 A1 | 11/2006 | Scarberry | |
| 2006/0283450 A1 * | 12/2006 | Shissler | A61B 5/4836 128/204.21 |
| 2007/0039374 A1 | 2/2007 | Borali | |
| 2007/0079982 A1 | 4/2007 | Laurent et al. | |
| 2007/0107737 A1 | 5/2007 | Landis et al. | |
| 2007/0110124 A1 | 5/2007 | Shiraki et al. | |
| 2007/0144519 A1 | 6/2007 | Henry et al. | |
| 2007/0157928 A1 | 7/2007 | Pujol et al. | |
| 2007/0169776 A1 | 7/2007 | Kepler et al. | |
| 2007/0175473 A1 | 8/2007 | Lewis et al. | |
| 2007/0193580 A1 | 8/2007 | Feldhahn et al. | |
| 2007/0248934 A1 | 10/2007 | Mosimann | |
| 2007/0272240 A1 | 11/2007 | Aylsworth et al. | |
| 2007/0284361 A1 | 12/2007 | Nadjafizadeh et al. | |
| 2008/0000474 A1 | 1/2008 | Jochle et al. | |

(56) References Cited

U.S. PATENT DOCUMENTS

| | | |
|---|---|---|
| 2008/0015257 A1 | 1/2008 | Grosskreutz et al. |
| 2008/0027344 A1 | 1/2008 | Terry |
| 2008/0028850 A1 | 2/2008 | Payton et al. |
| 2008/0051674 A1 | 2/2008 | Davenport et al. |
| 2008/0066741 A1 | 3/2008 | LeMahieu et al. |
| 2008/0066751 A1 | 3/2008 | Polacsek |
| 2008/0072900 A1 | 3/2008 | Kenyon et al. |
| 2008/0105257 A1 | 5/2008 | Klasek et al. |
| 2008/0142019 A1 | 6/2008 | Lewis et al. |
| 2008/0196716 A1* | 8/2008 | Wachter ............ A61M 15/0086 128/203.12 |
| 2008/0202512 A1 | 8/2008 | Kressierer |
| 2008/0205481 A1 | 8/2008 | Faries |
| 2008/0205979 A1 | 8/2008 | Gombert et al. |
| 2008/0207028 A1 | 8/2008 | Schutz |
| 2008/0251073 A1 | 10/2008 | Jassell et al. |
| 2008/0264413 A1 | 10/2008 | Doherty et al. |
| 2008/0302362 A1* | 12/2008 | Kwok ................... A61M 16/16 128/203.16 |
| 2008/0308169 A1 | 12/2008 | Nielsen |
| 2009/0041080 A1 | 2/2009 | Koch |
| 2009/0044808 A1 | 2/2009 | Guney et al. |
| 2009/0050150 A1 | 2/2009 | Rossen et al. |
| 2009/0056712 A1 | 3/2009 | Cortez, Jr. et al. |
| 2009/0056713 A1 | 3/2009 | Cortez, Jr. et al. |
| 2009/0078259 A1 | 3/2009 | Kooji et al. |
| 2009/0087259 A1 | 3/2009 | Kooji et al. |
| 2009/0107493 A1 | 4/2009 | Liu et al. |
| 2009/0107496 A1 | 4/2009 | McGhin et al. |
| 2009/0107501 A1 | 4/2009 | Krieger |
| 2009/0107981 A1 | 4/2009 | Andel et al. |
| 2009/0110022 A1 | 4/2009 | Snyder et al. |
| 2009/0110378 A1 | 4/2009 | Bradley et al. |
| 2009/0174092 A1 | 7/2009 | Kwok et al. |
| 2009/0180829 A1 | 7/2009 | Rejman et al. |
| 2009/0223514 A1 | 9/2009 | Smith et al. |
| 2009/0243226 A1 | 10/2009 | Liepold |
| 2009/0247989 A1 | 10/2009 | Burke |
| 2009/0301482 A1 | 12/2009 | Burton et al. |
| 2009/0320840 A1 | 12/2009 | Klasek et al. |
| 2010/0015830 A1 | 1/2010 | Simeon et al. |
| 2010/0083965 A1* | 4/2010 | Virr ................... A61M 16/0875 128/203.26 |
| 2010/0087749 A1 | 4/2010 | Tovey |
| 2010/0102799 A1 | 4/2010 | Schnidrig |
| 2010/0116272 A1 | 5/2010 | Row et al. |
| 2010/0147301 A1 | 6/2010 | Kwok |
| 2010/0154796 A1 | 6/2010 | Smith et al. |
| 2010/0204602 A1* | 8/2010 | Addington ............. A61M 11/02 600/538 |
| 2010/0242963 A1 | 9/2010 | Brieger et al. |
| 2010/0272507 A1 | 10/2010 | Khoe |
| 2010/0292601 A1 | 11/2010 | Dompeling et al. |
| 2011/0017212 A1 | 1/2011 | Kenyon et al. |
| 2011/0023874 A1 | 2/2011 | Bath et al. |
| 2011/0046433 A1 | 2/2011 | Khodak |
| 2011/0046494 A1 | 2/2011 | Balji et al. |
| 2011/0078109 A1 | 3/2011 | Mayer et al. |
| 2011/0088693 A1 | 4/2011 | Somervell et al. |
| 2011/0108031 A1 | 5/2011 | Korneff et al. |
| 2011/0114093 A1 | 5/2011 | Patil et al. |
| 2011/0155132 A1 | 6/2011 | Virr et al. |
| 2011/0180068 A1 | 7/2011 | Kenyon et al. |
| 2011/0186048 A1 | 8/2011 | Casse et al. |
| 2011/0247623 A1 | 10/2011 | McCarthy |
| 2011/0253136 A1 | 10/2011 | Sweeney et al. |
| 2011/0283999 A2 | 11/2011 | Smith et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0060838 A1 | 3/2012 | Lapoint et al. |
| 2012/0073573 A1 | 3/2012 | Thurdor et al. |
| 2012/0125333 A1 | 5/2012 | Bedford et al. |
| 2012/0125334 A1 | 5/2012 | Korneff et al. |
| 2012/0146251 A1 | 6/2012 | Heine et al. |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0255758 A1 | 10/2012 | Lee |
| 2012/0266880 A1* | 10/2012 | Young ............... A61M 16/0816 128/203.26 |
| 2012/0283570 A1 | 11/2012 | Tegg |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0079667 A1 | 3/2013 | Berkcan et al. |
| 2013/0081619 A1 | 4/2013 | Seakins et al. |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112201 A1 | 5/2013 | Graham et al. |
| 2013/0112202 A1 | 5/2013 | Fogelbrink |
| 2013/0152931 A1 | 6/2013 | Sims et al. |
| 2013/0174839 A1 | 7/2013 | Ging et al. |
| 2013/0199529 A1 | 8/2013 | Power et al. |
| 2013/0206140 A1 | 8/2013 | Kepler et al. |
| 2013/0237781 A1 | 9/2013 | Gyrn |
| 2013/0239960 A1 | 9/2013 | Bertinetti et al. |
| 2013/0239966 A1 | 9/2013 | Klasek et al. |
| 2013/0247905 A1 | 9/2013 | Miller et al. |
| 2013/0248044 A1 | 9/2013 | Shiga et al. |
| 2013/0252461 A1 | 9/2013 | Gross |
| 2013/0255677 A1 | 10/2013 | Varga |
| 2013/0333701 A1 | 12/2013 | Herron |
| 2013/0340752 A1 | 12/2013 | Landis et al. |
| 2014/0007872 A1 | 1/2014 | Grundler et al. |
| 2014/0020684 A1 | 1/2014 | Klasek et al. |
| 2014/0048065 A1* | 2/2014 | Haroutunian ..... A61M 15/0065 128/203.15 |
| 2014/0090649 A1 | 4/2014 | Groll et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0202462 A1 | 7/2014 | Stoks |
| 2014/0202463 A1 | 7/2014 | Ging et al. |
| 2014/0216446 A1 | 8/2014 | Wruck |
| 2014/0246021 A1 | 9/2014 | Buechi et al. |
| 2014/0251322 A1 | 9/2014 | Miller |
| 2014/0251331 A1 | 9/2014 | Korneff et al. |
| 2014/0283829 A1* | 9/2014 | Miller ................... A61M 16/04 128/203.14 |
| 2014/0311489 A1 | 10/2014 | Heine et al. |
| 2014/0318536 A1 | 10/2014 | Landis et al. |
| 2014/0331786 A1 | 11/2014 | Romano |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2015/0027204 A1 | 1/2015 | Stoks et al. |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0096560 A1 | 4/2015 | Klenner et al. |
| 2015/0107588 A1 | 4/2015 | Cheung et al. |
| 2015/0144130 A1 | 5/2015 | O'Donnell et al. |
| 2015/0196725 A1 | 7/2015 | Oates et al. |
| 2015/0359990 A1 | 12/2015 | Barker et al. |
| 2016/0008560 A1 | 1/2016 | Kwok |
| 2016/0015937 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0199612 A1 | 7/2016 | Foote et al. |
| 2016/0256642 A1 | 9/2016 | Soysa et al. |
| 2016/0256657 A1 | 9/2016 | Klasek et al. |
| 2016/0296721 A1 | 10/2016 | Landis et al. |
| 2016/0310691 A1 | 10/2016 | Bath et al. |
| 2016/0367776 A1 | 12/2016 | Landis et al. |
| 2016/0367779 A1 | 12/2016 | Landis et al. |
| 2017/0000968 A1* | 1/2017 | Harrington ......... A61M 16/026 |
| 2017/0095635 A1 | 4/2017 | Huby et al. |

(56) References Cited

U.S. PATENT DOCUMENTS

| | | | |
|---|---|---|---|
| 2017/0136198 | A1 | 5/2017 | Delangre et al. |
| 2017/0151411 | A1 | 6/2017 | Osborne et al. |
| 2017/0161461 | A1 | 6/2017 | Delangre et al. |
| 2017/0173293 | A1 | 6/2017 | Osborne et al. |
| 2017/0197057 | A1 | 7/2017 | Osborne et al. |
| 2017/0239432 | A1 | 8/2017 | Delangre et al. |
| 2017/0326320 | A1 | 11/2017 | Baigent et al. |
| 2018/0078730 | A1 | 3/2018 | Bath et al. |
| 2018/0169361 | A1 | 6/2018 | Dennis et al. |
| 2018/0214660 | A1 | 8/2018 | Stoks et al. |
| 2018/0250491 | A1 | 9/2018 | Row et al. |
| 2018/0296791 | A1 | 10/2018 | Klenner et al. |
| 2019/0255278 | A1 | 8/2019 | Osborne et al. |
| 2020/0061329 | A1 | 2/2020 | Mcintyre et al. |
| 2020/0101253 | A1 | 4/2020 | Osborne et al. |
| 2021/0220601 | A1 | 7/2021 | Stoks et al. |

FOREIGN PATENT DOCUMENTS

| | | |
|---|---|---|
| AU | 2000071791 | 3/2001 |
| AU | 2001/028104 | 9/2001 |
| AU | 2002244571 | 9/2002 |
| AU | 2007317198 | 5/2008 |
| AU | 2010206053 | 2/2011 |
| AU | 2013201490 | 4/2013 |
| CA | 1202862 | 4/1986 |
| CA | 2464530 | 5/2003 |
| CA | 2495451 | 3/2004 |
| CA | 2535974 | 10/2011 |
| CA | 2393743 | 1/2012 |
| CA | 2852215 | 4/2013 |
| CN | 2243015 | 12/1996 |
| CN | 1598510 | 3/2005 |
| CN | 1688358 | 10/2005 |
| CN | 101541367 | 9/2009 |
| CN | 101666664 | 3/2010 |
| CN | 102844645 A | 12/2012 |
| CN | 201672170 | 12/2015 |
| DE | 3110903 | 9/1982 |
| DE | 3618614 | 12/1987 |
| DE | 4020522 | 1/1992 |
| DE | 4102223 | 7/1992 |
| DE | 19647548 | 5/1998 |
| DE | 19958296 | 9/2001 |
| DE | 20 2004 006 484.7 | 9/2005 |
| DE | 1020040307 47 | 1/2006 |
| DE | 20 2005 008 152.3 | 10/2006 |
| DE | 20 2005 008 156.6 | 10/2006 |
| DE | 203 21 468.4 | 8/2007 |
| DE | 203 21 469.2 | 8/2007 |
| DE | 203 21 470.6 | 8/2007 |
| DE | 203 21 471.4 | 8/2007 |
| DE | 203 21 472.2 | 8/2007 |
| DE | 20 2006 007 397.3 | 9/2007 |
| DE | 20 2004 021 759.7 | 10/2007 |
| DE | 20 2006 011 754.7 | 12/2007 |
| DE | 201 22 844.0 | 5/2008 |
| DE | 102007003454 | 7/2008 |
| DE | 102007003455 | 8/2008 |
| DE | 102007039391 | 2/2009 |
| DE | 102008001022 | 10/2009 |
| DE | 20 2004 021 757.0 | 9/2010 |
| DE | 20 2004 021 758.9 | 9/2010 |
| DE | 201 22 937.4 | 9/2010 |
| DE | 20 2004 021 756.2 | 10/2010 |
| DE | 20 2004 021 774.0 | 11/2010 |
| DE | 20 2004 021 777.5 | 12/2010 |
| DE | 20 2004 021 794.5 | 2/2011 |
| DE | 20 2004 021 795.3 | 2/2011 |
| DE | 20 2004 021 796.1 | 2/2011 |
| DE | 20 2004 021 798.8 | 2/2011 |
| DE | 20 2006 020 951.4 | 2/2011 |
| DE | 20 2006 020 952.4 | 2/2011 |
| DE | 20 2004 021829.1 | 5/2011 |
| DE | 201 22 943.9 | 5/2011 |
| DE | 201 22 944.7 | 5/2011 |
| DE | 201 22 945.5 | 5/2011 |
| DE | 20 2005 021 927.4 | 6/2011 |
| DE | 20 2006 021 019.9 | 11/2011 |
| DE | 203 21 882.5 | 12/2011 |
| DE | 20 2004 021876.3 | 1/2012 |
| DE | 20 2007 019350.5 | 1/2012 |
| DE | 20 2011 107 902.7 | 1/2012 |
| DE | 20 2010 016 037.5 | 3/2012 |
| DE | 20 2012 007 229.3 | 10/2012 |
| EP | 0111248 | 6/1984 |
| EP | 0050984 | 12/1984 |
| EP | 0201985 | 11/1986 |
| EP | 0291921 | 11/1988 |
| EP | 0535952 | 4/1993 |
| EP | 0567158 | 10/1993 |
| EP | 0232864 | 5/1994 |
| EP | 0672430 | 9/1995 |
| EP | 0885623 | 12/1998 |
| EP | 1262208 | 12/2002 |
| EP | 1352670 | 10/2003 |
| EP | 1396277 | 3/2004 |
| EP | 1535722 | 6/2005 |
| EP | 1646910 | 4/2006 |
| EP | 1129743 | 5/2006 |
| EP | 1669098 | 6/2006 |
| EP | 1035887 | 7/2006 |
| EP | 1683066 | 7/2006 |
| EP | 1457223 B1 | 10/2006 |
| EP | 1741462 | 1/2007 |
| EP | 1837640 A2 | 9/2007 |
| EP | 1055431 | 11/2007 |
| EP | 1924311 | 5/2008 |
| EP | 1933914 | 6/2008 |
| EP | 1979030 | 10/2008 |
| EP | 2079505 | 7/2009 |
| EP | 2089086 | 8/2009 |
| EP | 2101851 | 9/2009 |
| EP | 2195061 | 6/2010 |
| EP | 2236167 | 10/2010 |
| EP | 2282795 | 2/2011 |
| EP | 2307082 | 4/2011 |
| EP | 2335761 | 6/2011 |
| EP | 2340867 | 7/2011 |
| EP | 2355881 | 8/2011 |
| EP | 2133611 | 9/2011 |
| EP | 2415445 | 2/2012 |
| EP | 2471568 | 7/2012 |
| EP | 2498854 | 9/2012 |
| EP | 2281138 B1 | 10/2012 |
| EP | 2514478 | 10/2012 |
| EP | 2575944 | 4/2013 |
| EP | 2629080 | 8/2013 |
| EP | 2640451 | 9/2013 |
| EP | 2651481 | 10/2013 |
| EP | 2654869 | 10/2013 |
| EP | 2667919 | 12/2013 |
| EP | 2522255 | 3/2014 |
| EP | 2703034 A2 | 3/2014 |
| EP | 2760516 | 8/2014 |
| EP | 2830695 | 2/2015 |
| EP | 2877224 | 6/2015 |
| EP | 3013402 | 5/2016 |
| EP | 1359962 | 8/2016 |
| EP | 3053623 | 8/2016 |
| EP | 3148418 | 4/2017 |
| EP | 3082920 | 10/2017 |
| EP | 3148419 | 1/2018 |
| GB | 1310949 | 3/1973 |
| GB | 1364127 | 8/1974 |
| GB | 2176313 | 12/1986 |
| GB | 2224957 | 5/1990 |
| GB | 2504284 A | 1/2014 |
| JP | 59113392 | 6/1984 |
| JP | H0623051 | 2/1994 |
| JP | 11033119 | 2/1999 |
| JP | 11286058 | 10/1999 |
| JP | 2001095920 | 4/2001 |
| JP | 2001-129091 A | 5/2001 |

(56) References Cited

FOREIGN PATENT DOCUMENTS

| | | |
|---|---|---|
| JP | 20011511507 | 8/2001 |
| JP | 2003139276 | 5/2003 |
| JP | 03194747 | 7/2003 |
| JP | 2003275312 | 9/2003 |
| JP | 2008132370 | 6/2008 |
| JP | 4242816 | 3/2009 |
| JP | 44022293 | 2/2010 |
| JP | 2011125618 | 6/2011 |
| JP | 11248076 | 12/2011 |
| JP | H 05208935 | 6/2013 |
| NZ | 564886 | 2/2011 |
| NZ | 587113 | 12/2011 |
| NZ | 586325 | 1/2012 |
| NZ | 583968 | 10/2012 |
| NZ | 597020 | 6/2013 |
| NZ | 600986 | 8/2013 |
| NZ | 604137 | 6/2014 |
| NZ | 610299 | 11/2014 |
| NZ | 630762 | 2/2016 |
| NZ | 625605 | 4/2016 |
| NZ | 710078 | 1/2017 |
| NZ | 710351 | 1/2017 |
| NZ | 631374 | 4/2017 |
| NZ | 631008 | 7/2017 |
| NZ | 733931 | 2/2019 |
| TW | 201245604 | 11/2012 |
| WO | WO 1996/020748 | 7/1996 |
| WO | WO 97/18001 | 5/1997 |
| WO | WO 1997/042475 | 11/1997 |
| WO | WO 2000/029057 | 5/2000 |
| WO | WO 2001/032069 | 5/2001 |
| WO | WO 01/41854 | 6/2001 |
| WO | WO 01/97894 | 12/2001 |
| WO | WO 2002/017991 | 3/2002 |
| WO | WO 02/066106 | 8/2002 |
| WO | WO 02/066107 | 8/2002 |
| WO | WO 2002/066106 | 8/2002 |
| WO | WO 2002/075854 | 9/2002 |
| WO | WO 2003/026721 | 4/2003 |
| WO | WO 2004/011072 | 2/2004 |
| WO | WO 2004/024429 | 3/2004 |
| WO | WO 2004/037330 | 5/2004 |
| WO | WO 2004/092955 | 11/2004 |
| WO | WO 2004/093954 | 11/2004 |
| WO | WO 2004/093954 A1 | 11/2004 |
| WO | WO 2004/093955 A1 | 11/2004 |
| WO | WO 2005/011785 | 2/2005 |
| WO | WO 2005/021076 | 3/2005 |
| WO | WO 2005/079670 A1 | 9/2005 |
| WO | WO 2006/017350 | 2/2006 |
| WO | WO 2006/019323 | 2/2006 |
| WO | WO 2007/019626 | 2/2007 |
| WO | WO 2007/043060 | 4/2007 |
| WO | WO 2007/051230 | 5/2007 |
| WO | WO 2008/055308 | 5/2008 |
| WO | WO 2008/056993 | 5/2008 |
| WO | WO 2008/058328 | 5/2008 |
| WO | WO 2008/060046 | 5/2008 |
| WO | WO 2008/060295 | 5/2008 |
| WO | WO 2008/076230 | 6/2008 |
| WO | WO 2008/097211 | 12/2008 |
| WO | WO 2009/002004 | 12/2008 |
| WO | WO 2009/006586 | 1/2009 |
| WO | WO 2009/022004 | 2/2009 |
| WO | WO 2009/127192 | 10/2009 |
| WO | WO 2009/146484 | 12/2009 |
| WO | WO 2010/031125 | 3/2010 |
| WO | WO 2010/031126 | 3/2010 |
| WO | WO 2010/091259 | 8/2010 |
| WO | WO 2011/030251 A1 | 3/2011 |
| WO | WO 2011/059622 | 5/2011 |
| WO | WO 2012/031315 A1 | 3/2012 |
| WO | WO 2012/053910 | 4/2012 |
| WO | WO 2012/065999 A2 | 5/2012 |
| WO | WO 2012/087644 | 6/2012 |
| WO | WO 2012/100291 | 8/2012 |
| WO | WO 2012/154883 | 11/2012 |
| WO | WO 2012/164407 | 12/2012 |
| WO | WO 2013/022356 A1 | 2/2013 |
| WO | WO 2013/026901 | 2/2013 |
| WO | WO 2013/162386 | 3/2013 |
| WO | WO 2013/045572 | 4/2013 |
| WO | WO 2013/045575 A1 | 4/2013 |
| WO | WO 2013/045586 | 4/2013 |
| WO | WO 2013/049660 | 4/2013 |
| WO | WO 2013/050907 | 4/2013 |
| WO | WO 2013/050907 A1 | 4/2013 |
| WO | WO 2013/088351 | 6/2013 |
| WO | WO 2013/127474 | 9/2013 |
| WO | WO 2013/137753 | 9/2013 |
| WO | WO 2013/151447 | 10/2013 |
| WO | WO 2013/162386 | 10/2013 |
| WO | WO 2014/015382 | 1/2014 |
| WO | WO 2014/055407 | 4/2014 |
| WO | WO 2014/077706 | 5/2014 |
| WO | WO 2014/138804 | 9/2014 |
| WO | WO 2014/138804 A1 | 9/2014 |
| WO | WO 2014/205513 | 12/2014 |
| WO | WO 2015/038013 A1 | 3/2015 |
| WO | WO 2015/060729 | 4/2015 |
| WO | WO 2015/119515 A1 | 8/2015 |
| WO | WO 2015/160268 | 10/2015 |
| WO | WO 2015/179916 | 12/2015 |
| WO | WO 2015/179916 A1 | 12/2015 |
| WO | WO 2016/042522 | 3/2016 |
| WO | WO 2016/089224 | 6/2016 |
| WO | WO 2016/139645 | 6/2016 |
| WO | WO 2017/027906 | 2/2017 |
| WO | WO 2017/126980 | 7/2017 |

OTHER PUBLICATIONS

The Pacific Energy Association Reporter, Summer Issue, 1992, vol. II, pp. 13-17.
Extended European Search Report for Application No. 15803457.9 dated Nov. 28, 2017, 8 pages.
Chinese Examination Report for Application No. 201580038988.3 dated Aug. 30, 2018.
ISR for International App No. PCT/NZ2013/000042 dated Jul. 9, 2013.
ISR for International App No. PCT/NZ2015/050011; dated Mar. 19, 2015, 4 pages.
ISR for International App No. PCT/NZ2014/000201, dated Jan. 13, 2015, 21 pages.
IPRP for International App. No. PCT/IB2012/001786, dated Aug. 9, 2016.
ISR for International App. No. PCT/IB2012/001786, dated Nov. 21, 2012.
IPRP for International App. No. PCT/NZ2013/000222, dated Jun. 9, 2015.
ISR for International App. No. PCT/NZ2017/050157, dated May 9, 2018, 10 pages.
ISR from International App No. PCT/NZ2013/000075 dated Jun. 24, 2013.
Sawyer, Dick, et al. "An introduction to human factors in medical devices." US Department of Health and Human Services, Public Health Service, Food and Drug Administration, Center for Devices and Radiological Health (1996).

* cited by examiner

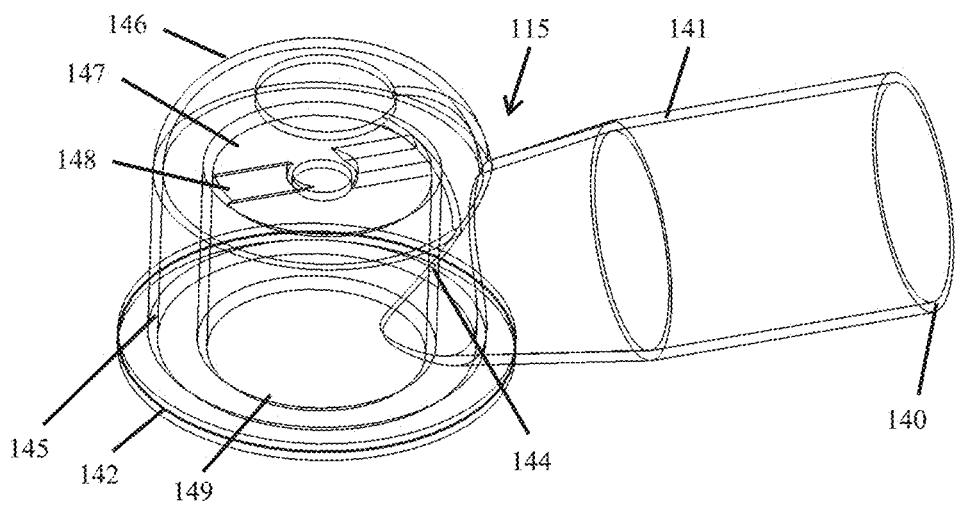
FIGURE 4A
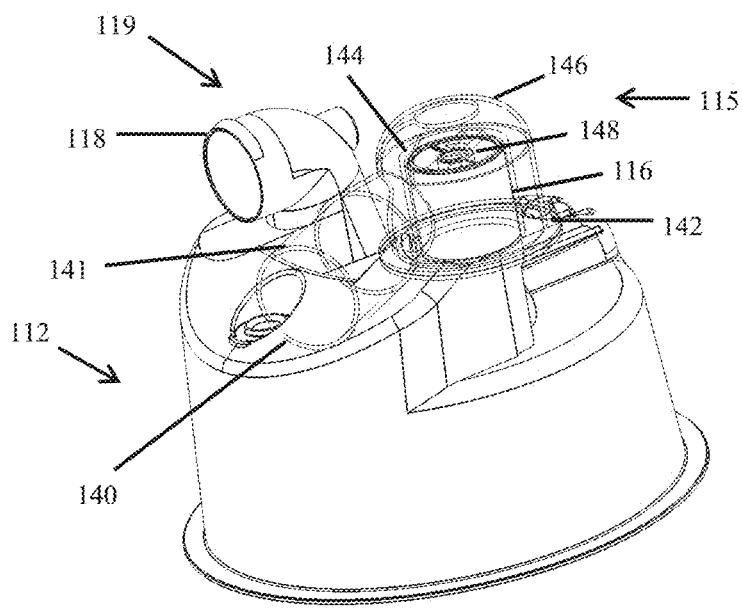
FIGURE 4B
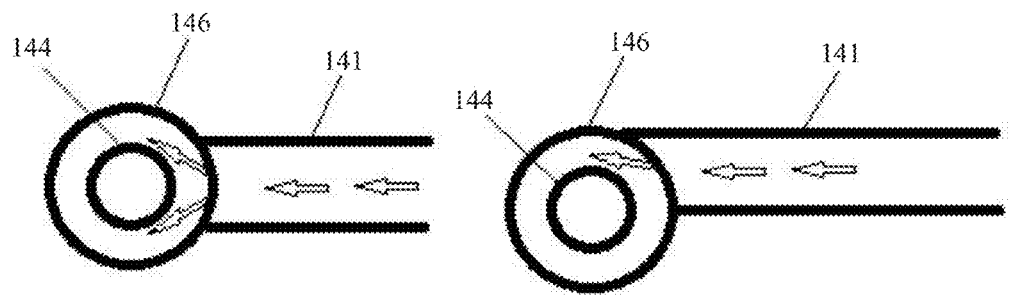
FIGURE 4C  FIGURE 4D

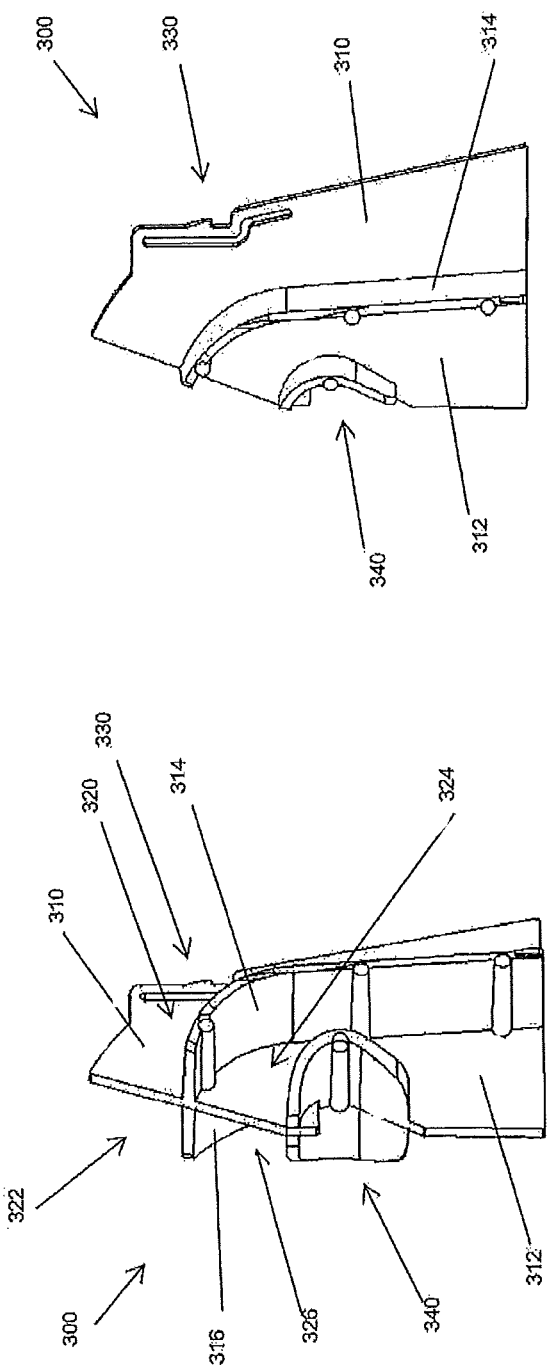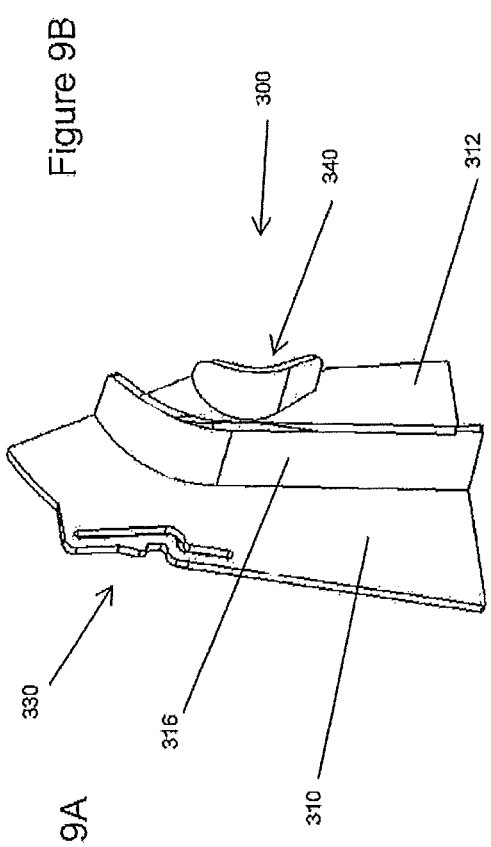

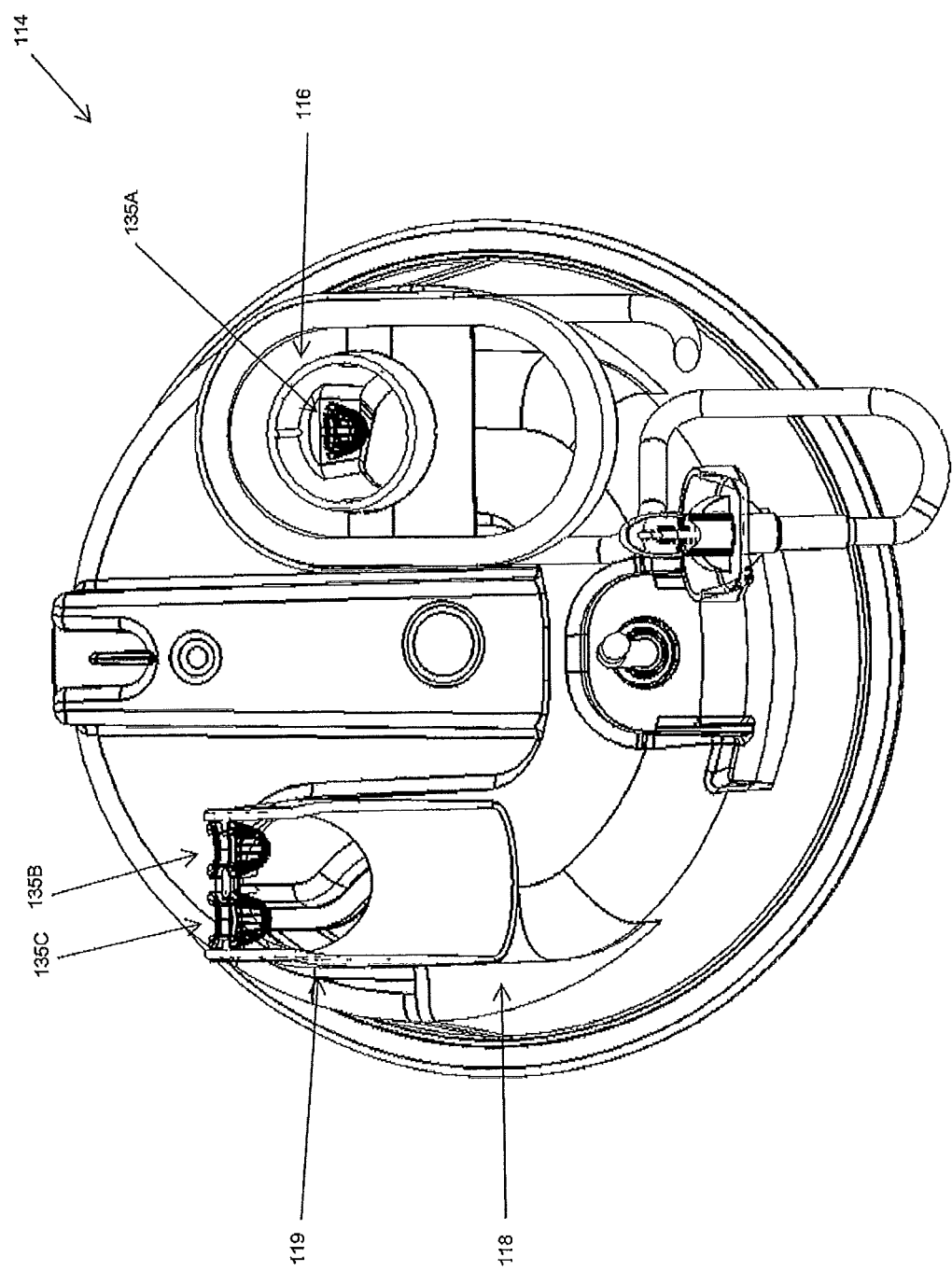

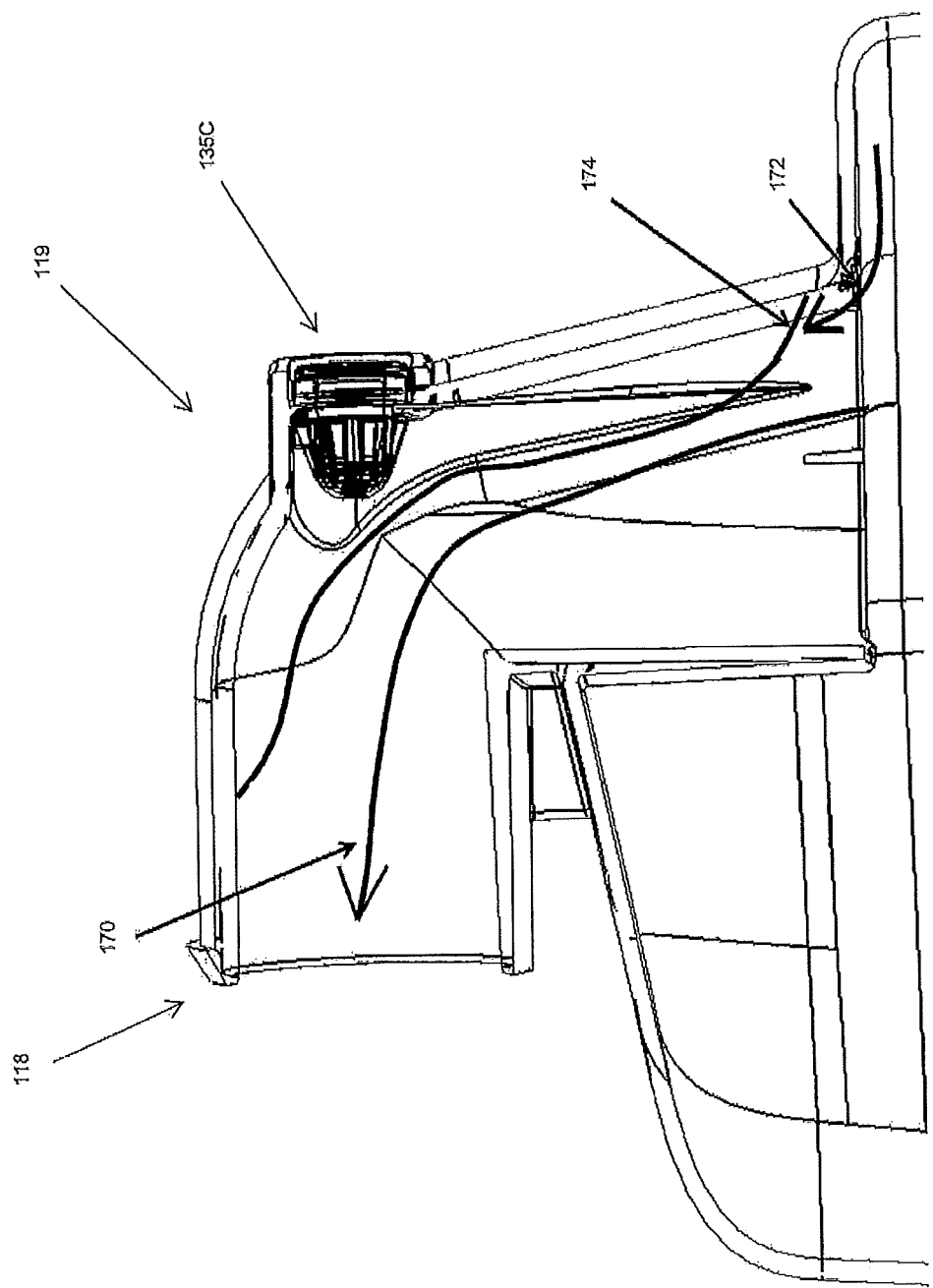

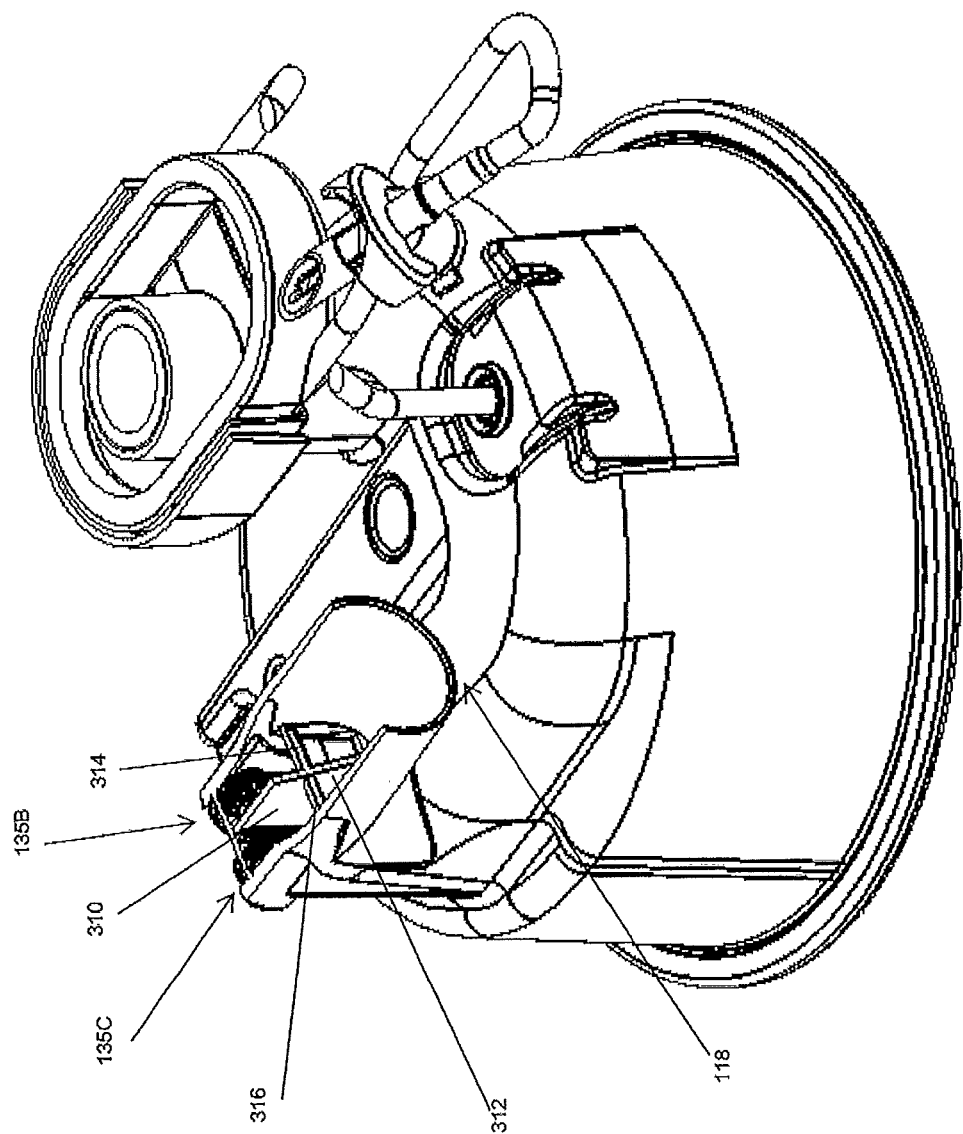

FLOW MIXERS FOR RESPIRATORY THERAPY SYSTEMS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to a respiratory therapy system. More particularly, certain features, aspects, and advantages of the present disclosure relate to a flow mixing or flow redistributing apparatus for use with a respiratory therapy system.

Description of Related Art

A respiratory therapy system may be used to provide respiratory gases to a patient. The respiratory therapy system may comprise a gases source, an interface that may be used to deliver gases to an airway of a patient, and a conduit extending between the gases source and the interface. The respiratory therapy system may also include a humidification apparatus to humidify and/or heat gases prior to delivery. Gases delivered to a patient at 100% relative humidity and 37° C. generally mimic properties of air resulting from the transformation that occurs as air passes through airways from the nose to the lungs. This can promote efficient gases exchange and ventilation in the lungs, aid defense mechanisms in the airways, and increase patient comfort during treatment. The humidification apparatus can include a water reservoir and a heating element for heating the water in the reservoir. As the water heats, vapor is formed that can humidify the gases flowing through the humidification apparatus. A humidification apparatus can also be utilized for other medical applications where heating and humidification of gases may be useful, including the insufflation gases used in laparoscopic surgery, for example but without limitation.

It can be useful to determine various characteristics of gases flowing through the respiratory therapy system, including flow rate and temperature. In some cases, numerical values associated with these characteristics can be used as inputs to, for example, a closed loop (for example, proportional-integral-derivative or PID) or open loop control system, which in turn can be used to guide operation of a mechanical blower or a humidification apparatus. However, achieving fine control with such control systems depends on the accuracy of the sensors used to determine such gases characteristics, as well as on the uniformity of the flow of gases. In some cases, the accuracy or precision of a sensor used to determine a characteristic of gases flowing through a gases passageway can be less than desirable if the characteristic occurs in a radially asymmetric pattern across a cross-section or profile of the gases passageway. For example, if gases flow through a gases passageway that comprises a bend, the velocity of the gases in the gases passageway can be radially asymmetric in a cross-section of the gases passageway at or near the bend or downstream of the bend, This variability of a given gases characteristic can undesirably affect the sensor accuracy, particularly if the number and severity of bends in the gases passageway in use will be unknown, as the magnitude of errors in output signals of the sensor used can be difficult to predict. Similarly, non-laminar flow (that is, turbulent flow) also can adversely impact the accuracy or precision of the reading from the sensor.

SUMMARY

Certain features, aspects, and advantages of at least one of the embodiments disclosed herein include the realization that mixing gases flowing through a gases passageway upstream of a sensor configured to measure of a characteristic of the gases can improve the accuracy of the sensor by improving uniformity in the flow along a cross-section or profile of the gases passageway. "Mixing" as used herein may be understood to refer to redistributing or conditioning a flow of gases that has been asymmetrically split along a first cross-section of a gases passageway into, for example, high-velocity components and low-velocity components, such that the velocity of the flow of gases after mixing may be more symmetric along a second cross-section of the gases passageway downstream of the first cross-section (as shown and described in FIG. 7 and elsewhere in this disclosure). The flow of gases may be mixed or made more homogenous to improve the accuracy of a sensor by positioning a static mixer or other mixing apparatus in the gases passageway upstream of the sensor, such that the mixer imparts a tangential, helical, swirling, or rotary motion to the flow of gases.

At least one aspect of the present disclosure relates to a flow mixer. The flow mixer comprises a static mixer. The flow mixer comprises a jacket adapted to be positioned in a gases passageway. At least one vane extends inwardly from the jacket. The at least one vane is configured to impart a tangential motion to gases flowing along the at least one vane.

Each vane of the flow mixer can extend inwardly or converge upon an internal center of the jacket. Each vane of the flow mixer can extend inwardly to a position at or near a central location equidistant from a first section of the jacket where the vane originates and a second section of the jacket opposite the first section. Each vane can support an internal conduit located at or near the central location. The vanes can be positioned such that they extend inwardly from the jacket at positions that are radially equidistant with respect to the inner surface of the jacket.

Each vane can extend axially along a length of the jacket. Each vane can extend axially along the entire length of the jacket. Each vane can extend spirally along a length of the jacket. Each vane can extend spirally along the entire length of the jacket. Each vane can extend axially and spirally along the length of the jacket. Each vane can extend along the length of the jacket at a constant pitch, Each vane can extend along the length of the jacket at a variable pitch.

The jacket can be cylindrical. The outer surface of the jacket can be smooth. The at least one vane of the flow mixer can comprise a plurality of vanes. A plurality of vanes can consist of, for example, two, three, or four vanes.

At least one aspect of the present disclosure relates to a respiratory therapy system, The respiratory therapy system comprises a gases passageway adapted to transmit gases to a patient and a flow mixer positioned in the gases passageway. The flow mixer can, for example, comprise one of the flow mixer configurations described above or elsewhere in this specification.

A sensor can be positioned in a section of the gases passageway downstream of the flow mixer. The sensor can comprise a temperature sensor and/or a flow sensor. A humidification apparatus can be located downstream of the flow mixer. A flow generator can be located upstream of the flow mixer. A patient interface can be located downstream of the flow mixer and/or downstream of the gases passageway.

At least one aspect of the present disclosure relates to a flow mixing apparatus for a respiratory therapy system. The flow mixing apparatus comprises a cap comprising a first end adapted to be placed over and/or into an inlet of a gases passageway, a second end having an aperture, and a side wall extending between the first and second ends. A gases compartment surrounds the side wall and second end of the cap. The gases compartment comprises a channel adapted to admit a flow of gases. The flow mixing apparatus is configured such that gases flowing through the channel are directed around the side wall and into the second end.

The edges of the aperture can be beveled. The gases compartment and the cap can be integrally formed or be in the form of a single continuous part. The channel can be oriented with respect to the cap such that in use a flow of gases through the channel can be perpendicular to a flow of gases through the aperture.

At least one aspect of the present disclosure relates to an alternative respiratory therapy system. The respiratory therapy system comprises a gases passageway adapted to transmit gases to a subject, the gases passageway comprising an inlet, and a flow mixing apparatus. The flow mixing apparatus comprises a cap comprising a first end adapted to be placed over and/or into the inlet of the gases passageway. The flow mixing apparatus can, for example, comprise one of the flow mixing apparatus configurations described above or elsewhere in this specification.

A flow mixer can be positioned in the gases passageway downstream of the cap. The flow mixer can, for example, comprise one of the flow mixer configurations described above or elsewhere in this specification.

At least one aspect of the present disclosure relates to a respiratory therapy apparatus comprising a gas flow path that comprises an gases inlet opening and a gases outlet opening. A flow conditioner is positioned along the gas flow path between the gases inlet opening and the gases outlet opening. The flow conditioner comprises at least one internal wall. The at least one internal wall divides the gases flow path into a first gases flow path and a second gases flow path at a location between the gases inlet opening and the gases outlet opening such that a plurality of compartments are defined within the gases flow path.

The plurality of compartments can be configured to promote laminar flow through at least one of the plurality of compartments. At least one sensor can be configured to sense flow through one of the plurality of compartments with the sensor sensing flow through the at least one of the plurality of compartments that is configured to promote laminar flow. The sensor can be sensitive to changes in flow velocity.

The gas flow passage can comprise a port of a humidifier. The gas flow passage can comprise an elbow-shaped port of the humidifier. The at least one internal wall can be non-linear. The at least one internal wall can comprise a pair of walls. The pair of walls can be concentric. Each of the pair of concentric walls can be adapted to guide flow passing from the gases inlet opening to the gases outlet opening.

The flow conditioner can be removable from the gases flow path. The flow conditioner can comprise a retainment feature that interfaces with a complementary feature in a wall defining at least a portion of the gases flow path. The flow conditioner can be snap fit to the wall defining at least the portion of the gases flow path.

The plurality of compartments can comprise four compartments. The flow conditioner can comprise four baffles that at least partially define four compartments.

The gases flow path can form a portion of a humidification chamber.

DESCRIPTION OF THE DRAWINGS

Specific embodiments and modifications thereof will become apparent to those skilled in the art from the detailed description herein having reference to the figures that follow.

FIG. 4A shows the flow mixing apparatus of FIG. 3.

FIG. 4B shows the flow mixing apparatus of FIG. 4A connected to the humidification chamber of FIG. 3, FIG. 4C shows a first example schematic of a gases flow path through the flow mixing apparatus of FIG. 3.

FIG. 4D shows a second example schematic of a gases flow path through the flow mixing apparatus of FIG. 3.

FIGS. 9A-9G show various views of an example embodiment of a flow conditioner configured to be disposed in an elbow-shaped outlet port of the humidification chamber.

FIG. 10 shows a section view of the humidification chamber having an elbow-shaped outlet port.

FIG. 11 shows flow through the elbow-shaped outlet port without use of the flow conditioner of FIGS. 9A-9G.

FIGS. 14A-14J show various section views of the flow conditioner disposed in the elbow-shaped outlet port of the humidification chamber.

DETAILED DESCRIPTION

Figure 1:
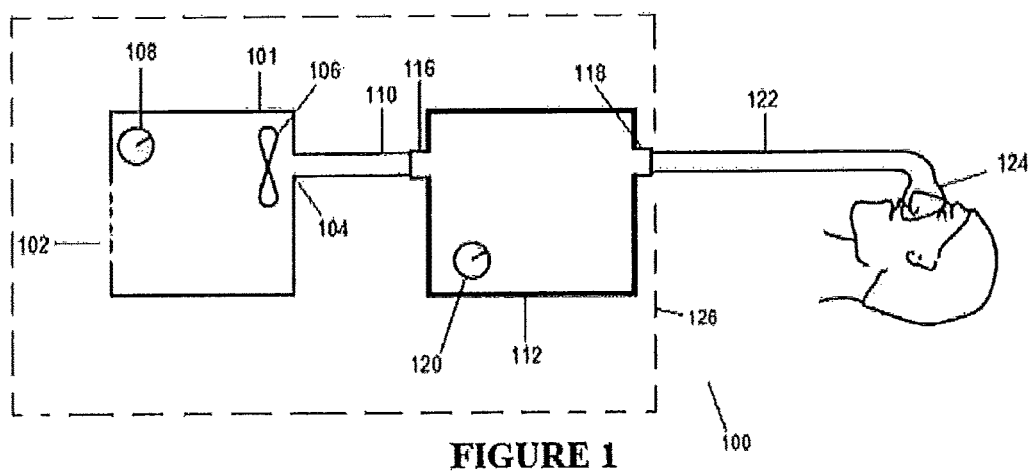
FIG. 1 shows a schematic diagram of an example configuration for a respiratory therapy system.

FIG. 1 shows a schematic diagram of an example configuration for a respiratory therapy system 100, In the illustrated configuration, the respiratory therapy system 100 may comprise a flow generator 101. The flow generator 101 may comprise a gases inlet 102 and a gases outlet 104. The flow generator 101 may comprise a blower 106. The blower 106 may comprise a motor. The motor may comprise a stator and a rotor. The rotor may comprise a shaft. An impeller may be linked to the shaft. In use, the impeller may rotate concurrently with the shaft to draw gases into the flow generator 101 through the gases inlet 102. As illustrated in FIG. 1, gases can be drawn into the flow generator 101 from the surrounding atmosphere, also known as room or ambient air. The flow generator 101 may comprise a user interface 108 that comprises one or more buttons, knobs, dials, switches, levers, touch screens, speakers, displays, and/or other input or output modules that may enable a user to operate the flow generator 101 and/or other components or aspects of the respiratory therapy system 100. The flow generator 101 may deliver gases through the gases outlet 104 to a first conduit 110. The first conduit 110 may deliver the gases to a humidification apparatus 112 that may be used to heat and/or humidify the gases.

The humidification apparatus 112 may comprise a humidifier inlet 116 and a humidifier outlet 118. The humidification apparatus 112 can be configured to hold water or another humidifying liquid (hereinafter referred to as water). The humidification apparatus 112 may also comprise a heater that may be used to heat the water held in the humidification apparatus 112 to add vapor to, and/or to increase the temperature of, gases flowing through the humidification apparatus 112 from the humidifier inlet 116 to the humidifier outlet 118. The heater may comprise, for example, a resistive metallic heating plate. The humidification apparatus 112 may comprise a user interface 120 that comprises one or more buttons, knobs, dials, switches, levers, touch screens, speakers, displays and/or other input or output modules that may enable a user to operate the humidification apparatus 112 and/or other components or aspects of the respiratory therapy system 100. Other configurations of the humidification apparatus 112 are possible and are intended to be included in the scope of this disclosure.

Gases may flow from the humidifier outlet 118 to a second conduit 122. The second conduit 122 may comprise a conduit heater. The conduit heater may be used to add heat to gases flowing through the second conduit 122, which may reduce or eliminate the likelihood of condensation of vapor held in humidified gases. The conduit heater may comprise one or more resistive wires located in, on, around, or near a wall of the second conduit 122 or in a gases flow path within the second conduit 122. Gases may flow from the second conduit 122 to a patient interface 124 that can pneumatically link the respiratory therapy system 100 to an airway of a patient. The patient interface 124 may be a sealing or non-sealing interface and may comprise a nasal mask, an oral mask, an oronasal mask, a full face mask, a nasal pillows mask, a nasal cannula, an endotracheal tube, a combination of the above, or some other gas conveying system or apparatus.

In the illustrated configuration, and as implied above, the respiratory therapy system 100 may operate as follows. Gases may be drawn into the flow generator 101 through the gases inlet 102 due to the rotation of an impeller of the motor of the blower 106. The gases may be propelled out of the gases outlet 104 and along the first conduit 110. The gases may enter the humidification apparatus 112 through the humidifier inlet 116. Once in the humidification apparatus 112, the gases may entrain moisture, or become more humidified, when flowing over or near water in the humidification apparatus 112. The water may be heated by the heater of the humidification apparatus 112, which may aid in the humidification and/or heating of the gases flowing through the humidification apparatus 112. The gases may leave the humidification apparatus 112 through the humidifier outlet 118 to the second conduit 122. Gases may flow from the second conduit 122 to the patient interface 124 and into an airway of a patient. To summarize, in use, gases may flow along a gases flow path extending from the gases inlet 102 of the flow generator 101 to the patient interface 124.

"Gases flow path" as used herein may refer to this entire gases flow path or a portion of such.

The illustrated configuration is not be taken to be limiting. Many other configurations for the respiratory therapy system 100 are possible. In some configurations, the flow generator 101 may, for example, comprise a source or container of compressed gases (for example, air or oxygen). A container of compressed gases may comprise a valve that may be adjusted to control a flow of gases leaving the container. In some configurations, the flow generator 101 may use such a source of compressed gases and/or another gases source in lieu of the blower 106. In some configurations, the blower 106 may be used in conjunction with another gases source. In some configurations, the blower 106 may comprise a motorized blower or may comprise a bellows or some other apparatus configured to generate a flow of gases. In some configurations, the flow generator 101 may draw in atmospheric gases through the gases inlet 102. In some configurations, the flow generator 101 may be adapted both to draw in atmospheric gases through the gases inlet 102 and to take in other gases (for example, oxygen, nitric oxide, or carbon dioxide) through the same gases inlet 102 or a different gases inlet. In some configurations, the flow generator 101 and the humidification apparatus 112 may be integrated or may share a housing 126. In some configurations, the flow generator 101 and the humidification apparatus 112 may be separate of each other and connected with a conduit, a duct or any other suitable manner of transmitting a gas flow from the flow generator 101 to the humidification apparatus 112 or from the humidification apparatus 112 to the flow generator 101.

In some configurations, the respiratory therapy system 100 may comprise a user interface located on the flow generator 101, the humidification apparatus 112, the first conduit 110, the second conduit 122, the patient interface 124, or another component of the respiratory therapy system 100. In some configurations, the operation of components or aspects of the respiratory therapy system 100 may be controlled wirelessly through a user interface located on a remote computing device such as a tablet, a mobile phone, a personal digital assistant, or another computing device. In some configurations, the operation of the flow generator 101, the humidification apparatus 112, or other components or aspects of the respiratory therapy system 100 may be controlled by a controller. The controller may comprise a microprocessor. The controller may be located in or on the flow generator 101, the humidification apparatus 112, or another component of the respiratory therapy system 100 or on a remote computing device. In some configurations, the operation of the flow generator 101, the humidification apparatus 112, or other components or aspects of the respiratory therapy system 100 may be controlled by multiple controllers.

In some configurations, the respiratory therapy system 100 may comprise one or more sensors configured to detect various characteristics of gases in the respiratory therapy system 100, including pressure, flow rate, temperature, absolute humidity, relative humidity, enthalpy, oxygen concentration, and/or carbon dioxide concentration; one or more sensors configured to detect various medical characteristics of the patient, including heart rate, EEG signal, EKG/ECG signal, blood oxygen concentration, blood $CO_2$ concentration, and/or blood glucose; and/or one or more sensors configured to detect various characteristics of gases or other substances outside the respiratory therapy system 100, including ambient temperature and/or ambient humidity. One or more of the sensors may be used to aid in the control of components of the respiratory therapy system 100, including the humidification apparatus 112, through the use of a closed or open loop control system (for example, through the use of the controller mentioned above).

In some configurations, there may be no user interface or a minimal user interface for components of the respiratory therapy system 100. In some such configurations, the respiratory therapy system 100 may utilize a sensor to detect that a patient is attempting to use the respiratory therapy system 100 and to automatically operate (for example, the flow generator 101 may generate a gases flow, and/or the humidification apparatus 112 may humidify gases, as previously described) according to one or more predetermined control parameters. In some configurations, the respiratory therapy system 100 may comprise a single limb circuit that comprises an inspiratory gases passageway. In some configurations, the respiratory therapy system 100 may comprise a dual limb system that comprises inspiratory and expiratory gases passageways.

The respiratory therapy system 100 may be used for other medical applications not involving providing gases to an airway of a patient. For example, the respiratory therapy system 100 could be used to provide insufflation gases for laparoscopic surgery. This application may be practiced by replacing the patient interface 124 with a surgical cannula that may be inserted into an abdominal cavity of a patient through an opening created, for example, using a trocar. Additionally, certain features, aspects, and advantages of embodiments of the present disclosure may be utilized for other applications involving the humidification of gases, including room humidifiers.

Figure 2:
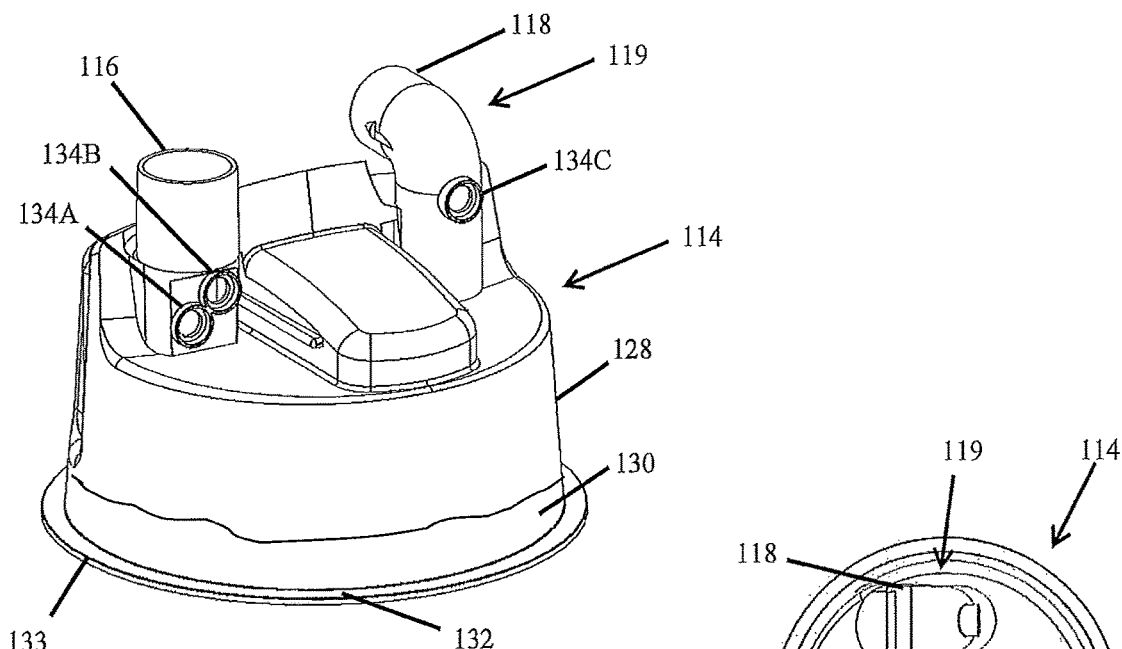
FIG. 2 shows a perspective view of a humidification chamber.

FIG. 2 shows a humidification chamber 114 that may comprise a part of the humidification apparatus 112. The humidification chamber 114 may comprise the humidifier inlet 116, the humidifier outlet 118, and a reservoir 128. As implied in the above description, gases flowing through the humidification apparatus 112 may flow through the humidifier inlet 116 and into the reservoir 128 that may contain a liquid 130 such as water. Humidified gases may flow from the reservoir 128 through the humidifier outlet 118. In the illustrated configuration, the humidifier inlet 116 extends in a linear manner while the humidifier outlet 118 extends in a nonlinear manner. The humidifier inlet 116 extends vertically. The humidifier outlet 118 extends vertically and then horizontally.

The humidification chamber 114 may comprise a base plate 132 that at least partially defines the reservoir 128. The base plate 132 may comprise a flange 133. The flange 133 may help to secure the humidification chamber 114 to a housing (not shown) of the humidification apparatus 112 having a complementary recess adapted to accept the flange 131 A heater (not shown) of the humidification apparatus 112 may be positioned under the base plate 132 to heat the water 130 in the reservoir 128, which may vaporize the water 130 to humidify the flow of gases, as well as increase the gases temperature. Other locations for a heater are possible, such as, for example, on or near the external or internal walls of the humidification chamber 114 or within the reservoir 128.

Sensors (not shown) may be positioned in apertures 134A, 134B, 134C located along the gases flow path extending between the humidifier inlet 116 and the humidifier outlet 118. The sensors may comprise, for example, flow sensors, temperature sensors, and/or humidity sensors that are configured to measure characteristics of gases flowing through the humidification chamber 114 before and/or after flowing through the reservoir 128. In the illustrated configuration, the humidifier inlet 116 has two apertures 134A, 134B while the humidifier outlet 118 has one aperture 134C. In some configurations, the humidifier inlet 116 has one aperture while the humidifier outlet 118 has two apertures. In some configurations, a sensor configured to be positioned in one of the apertures 134A, 134B, 134C can be a thermistor adapted to sense the temperature of gases passing within the flow path into which the thermistor extends. In some configurations, a pair of sensors configured to be positioned in any two of the apertures 134A, 134B, 134C can be a pair of thermistors where one or both of the thermistors is adapted to sense the temperature of gases passing within the flow path into which the thermistor(s) extend. In some configurations, a pair of sensors configured to be positioned in any two of the apertures 134A, 134B, 134C can be a pair of thermistors where one of the pair of thermistors is adapted to act as a reference and the pair of thermistors is adapted to sense the flow rate of gases passing within the flow path into which the pair of thermistors extend.

Figure 3:
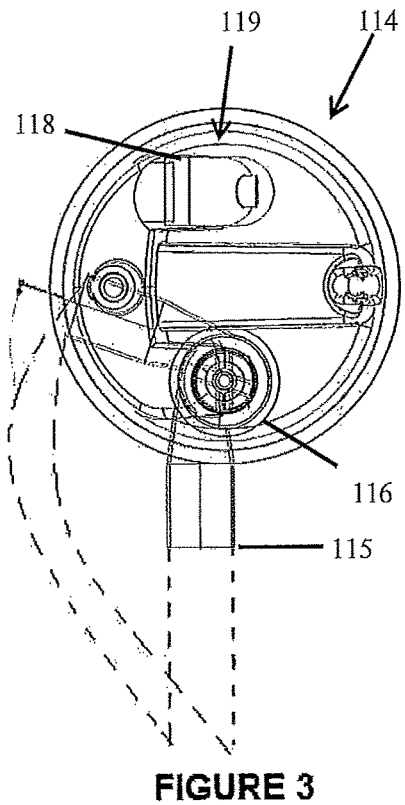
FIG. 3 shows a top-down view of the humidification chamber of FIG. 2 and a flow mixing apparatus.

FIG. 3 shows a top-down view of an embodiment of the humidification chamber 114 similar to that shown in FIG. 2 This embodiment of the humidification chamber 114 may similarly comprise the humidifier inlet 116 and the humidifier outlet 118. The humidification chamber 114 may also comprise a conduit connector 115 adapted to connect the first conduit 110 to the humidifier inlet 116. The conduit connector 115 may be configured to swivel, pivot, or otherwise move to allow the first conduit 110 to be oriented in a plurality of positions with respect to the humidification chamber 114. For example, as illustrated by the dotted lines representing the first conduit 110 in FIG. 3, the conduit connector 115 may be permitted to swivel around the humidifier inlet 116 to accommodate the position or orientation of the first conduit 110 with respect to the humidification chamber 114. However, although it is advantageous to allow flexibility in the position of the first conduit 110, as previously described, a bend in the first conduit 110 can adversely affect the accuracy of a sensor positioned downstream of the first conduit 110 by changing the velocity of the flow along a given cross-section or profile of the gases passageway of the first conduit 110. A bend, for example, may encompass a deviation in the angle of a conduit from greater than 0° to 180°, or from 30° to 150°, or from 60° to 120°. It may be advantageous to mix gases flowing through or from the first conduit 110 to counteract sensor inaccuracies caused by a bend in the first conduit 110.

FIGS. 4A and 4B illustrates a configuration for the conduit connector 115 that may improve flow mixing. The conduit connector 115 may be configured to induce a tangential or swirling motion to the flow—in other words, it may act as a flow mixer. As illustrated, the conduit connector 115 may comprise a connector inlet 140 adapted to receive gases from, for example, the first conduit 110. The connector inlet 140 may direct the received gases through a channel 141 leading to a gases compartment 146 that comprises a base 142. A cap 144 may be positioned within the gases compartment 146. A cavity may be present between the cap 144 and the gases compartment 146 to allow for the flow of gases through the conduit connector 115. The cap 144 may comprise an open end 149 configured to be placed over the inlet of a gases passageway, for example the humidifier inlet 116. In some configurations, the cap 144 may be configured to be placed into the humidifier inlet 116 instead of or in addition to being placed over the humidifier inlet 116. The cap 144 may be integrally formed or be in the form of a single continuous piece with the base 142. The cap 144 may comprise a sidewall 145 and a top 147. The top 147 may comprise apertures 148. The edges of the apertures 148 may be beveled or angled so as to direct gases flowing through the apertures axially and/or tangentially through the top 147. In some configurations, the beveled edges or other sections of the top 147 may comprise vanes that protrude down into the cap 144, the vanes extending axially and/or spirally to promote further gases mixing. In some configurations, the apertures 148 may comprise one aperture, a pair of apertures, or more than two apertures. In some configurations, the top 147 may not be present and the cap 144 may simply comprise two open ends.

In use, gases flowing through the channel 141 may be forced to flow along the sidewall 145 of the cap 144. Some gases may be forced to flow around or circumscribe the cap 144 and some gases may be forced to flow up the sidewall 145 to enter the apertures 148 and ultimately flow through the open end 149. The tangential velocity component of the gases may increase as a result of the motion of the flow of gases around the sidewall 145, which may improve the mixing of the gases. Additionally, gases circumscribing or flowing around the cap 144 may collide with gases flowing up the sidewall 145 and proceeding to the open end 149, which may increase gases mixing as a result of increased turbulence. In some configurations, and as seen in FIG. 4A, 4B, and most clearly in FIG. 4C, the channel 141 may be positioned such that gases flowing through the channel 141 strike the sidewall 145 of the cap 144 roughly head-on and are diverted clockwise or counterclockwise around the sidewall 145 with roughly equal biases. However, in some configurations, and as shown in FIG. 4D, the channel 141 may be positioned such that it is offset with respect to the cap 144. Gases flowing through the channel 141 may then be biased towards a side of the sidewall 145, which may further promote tangential motion of the gases.

FIGS. 5A-5G depict various configurations of flow mixers that embody other methods for mixing a gases flow by imparting a tangential, rotational, spiraling, swirling, or other motion to the gases flow that may be inserted or positioned in a gases passageway. The gases passageway may comprise, for example, the humidifier inlet 116 or the humidifier outlet 118. The flow mixer may comprise a static mixer. A "static mixer" may be understood as referring to a structure having no moving parts that promotes the mixing of gases or other fluids by utilizing the energy of the gases rather than utilizing energy from another source, such as an electrical power supply.

Figure 5A:
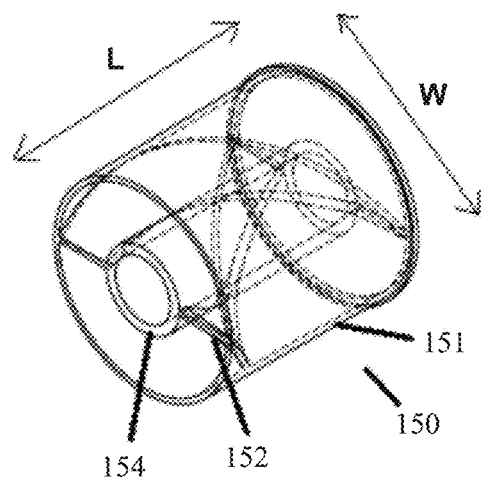
FIGS. 5A-5G show different embodiments of flow mixers.
Figure 5B:
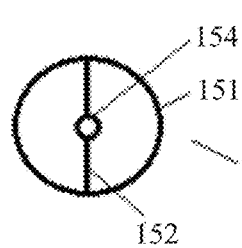
Figure 5C:
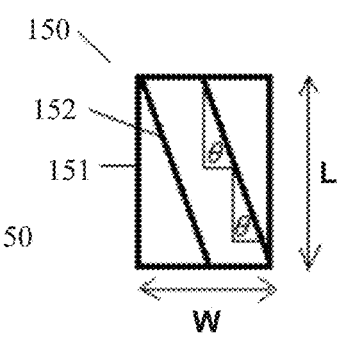

FIGS. 5A-5B show perspective and top-down views, respectively, of a flow mixer 150. The flow mixer 150 may be configured to impart a tangential, rotational, swirling, or spiral velocity vector to the gases flowing through the flow mixer 150. The flow mixer 150 may comprise a jacket 151. The profile or shape of the jacket 151 may match the profile or shape of the gases passageway in which the flow mixer 150 is placed. For example, the jacket 151 may be cylindrical. The jacket 151 may be smooth to facilitate insertion into and/or removal from the gases passageway. A pair of vanes 152 may extend inwardly from the jacket 151 towards a center of the flow mixer 150. In other words, each of the vanes 152 may extend inwardly from the jacket 151 to a location at or near a central location equidistant from a first section of the jacket 151 where the vane 152 originates and a second section of the jacket 151 opposite the first section. The vanes 152 may support an internal conduit 154 that may be centrally located in the flow mixer 150 and that may extend axially along the length of the flow mixer 150. In some embodiments, the internal conduit 154 may provide a passageway through which water may flow, for example, into a reservoir of a humidification apparatus. The internal conduit 154 may be sized or configured so as to accept a spike connected to a water source. In some embodiments, the internal conduit 154 may be sized or configured so as to accept a float retention apparatus that may extend through a gases passageway in which the flow mixer 150 is placed, such as the humidifier inlet 116.

As illustrated in FIGS. 5A-5B, the vanes 152 may extend axially and spirally along the length of the flow mixer 150 (and the jacket 151). As gases flow along the vanes 152, the gases may be guided in such a way that a part of the axial and/or radial components of the flow velocity vector may be modified to increase the tangential component of the flow velocity vector. The vanes 152 may each be angled such that they spirally traverse at least a portion or, in some embodiments, all of the length of the flow mixer 150 without intercepting each other (that is, the vanes 152 do not intersect in some embodiments). The angles of the vanes 152 may be such that the starting position of a given one of the vanes 152 is circumferentially offset by 180° from the ending position of the vane 152. The vanes 152 may have a constant pitch along the length of the vanes 152. In other words, each of the vanes 152 may extend spirally along the length of the jacket 151 such that the angle between any two points along the edge of the vane 152 is constant. The flow mixer 150 may be sized such that it can be easily inserted into a gases passageway. For example, the width of the flow mixer 150 (as shown by the double-ended arrow annotated 'W' in FIG. 5A) may be 10 mm to 30 mm, or 15 mm to 25 mm, or 20 mm. Similarly, the length of the flow mixer 150 (as shown by the double-ended arrow annotated 'L' in FIG. 5A) may be 10 mm to 30 mm, or 15 mm to 25 mm, or 20 mm. The angle of each of the vanes 152 may be, for example, 42° to 70°, or 46° to 66°, or 50° to 62°, or 54° to 58°, or 56°.

Figure 5D:
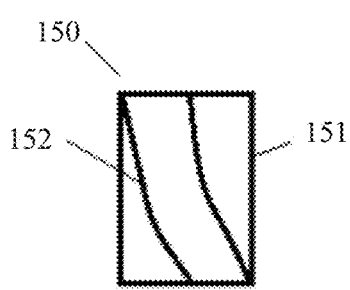
Figure 5E:
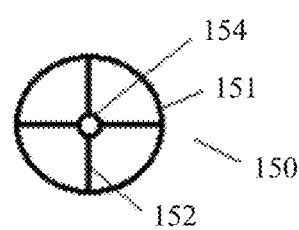

Other configurations for the flow mixer 150 are contemplated. For example, although FIGS. 5A and 5B illustrate that the pitch of the vanes 152 may be constant (more clearly shown in FIG. 5C through the use of the character θ), as illustrated in FIG. 5D the pitch of the vanes 152 may be variable across any portion of the length of the jacket 151. Additionally, although FIGS. 5A and 5B illustrate that the flow mixer 150 may comprise two vanes 152, in some configurations, a single vane 152 may be used, or more than two vanes 152 could be used. For example, FIG. 5E shows an embodiment of the flow mixer 150 comprising four vanes 152. Although FIGS. 5B and 5E, for example, show that the flow mixer 150 may comprise the internal conduit 154, in some configurations the internal conduit 154 may not be present, and the radial ends of the vanes 152 may touch at or near the center of the flow mixer 150. Although FIGS. 5B and 5E, for example, show that the vanes 152 may extend inwardly from the jacket 151 evenly (for example, that the vanes 152 may be positioned such that they extend inwardly from the jacket 151 at positions that are radially equidistant with respect to the inner surface of the jacket 151), in some configurations the vanes 152 may be staggered. Although FIG. 5A, for example, shows that the vanes 152 may extend along the entire length of the jacket 151, in some configurations the vanes 152 may extend only partially along the length of the jacket 151, and may begin or end at locations other than the axial ends of the jacket 151.

Figure 5F:
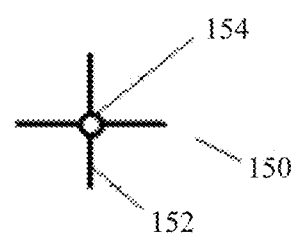
Figure 5G:
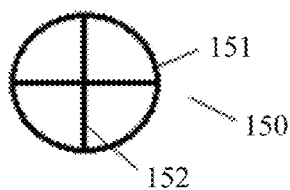

The vanes 152 may be different or have different characteristics from each other. For example, some of the vanes 152 may extend spirally across the entire length of the jacket 151 and some of the vanes 152 may only extend partially across the length of the jacket 151. In some configurations, and as illustrated in FIG. 5G, the internal conduit 154 may not be present. Although in some configurations the flow mixer 150 comprises the jacket 151, in some configurations, and as illustrated in FIG. 5F, the flow mixer 150 may not comprise a jacket. In some such configurations, if the flow mixer 150 does not comprise a jacket, the vanes 152 may fit in a gases passageway (for example, the humidifier inlet 116 or the humidifier outlet 118). In some configurations, the vanes 152 can be secured through a frictional fit and/or the ends of the vanes 152 may fit into corresponding recesses or catches on the inner surface of, for example, the humidifier inlet 116, or be secured or fixed using other retaining elements. The ends of the vanes 152 may, for example, be beveled such that they can slide into such recesses when the flow mixer 150 is pushed into the humidifier inlet 116 or the humidifier outlet 118.

In some configurations, the flow mixer 150 can be integrally moulded with a gases conduit (for example, the humidifier inlet 116 or the humidifier outlet 118), or the flow mixer 150 (which may or may not include the jacket 151) and the gases conduit can together otherwise be in the form of a single part or piece. Many other configurations are possible. Preferably, the flow mixer 150 may be configured to impart a tangential, rotational, swirling, or spiraling motion to a gases flow through the flow mixer 150 sufficient to reduce the error of sensors positioned downstream of the flow mixer 150 in a gases passageway while minimizing pressure loss of the gases flow.

Figure 6:
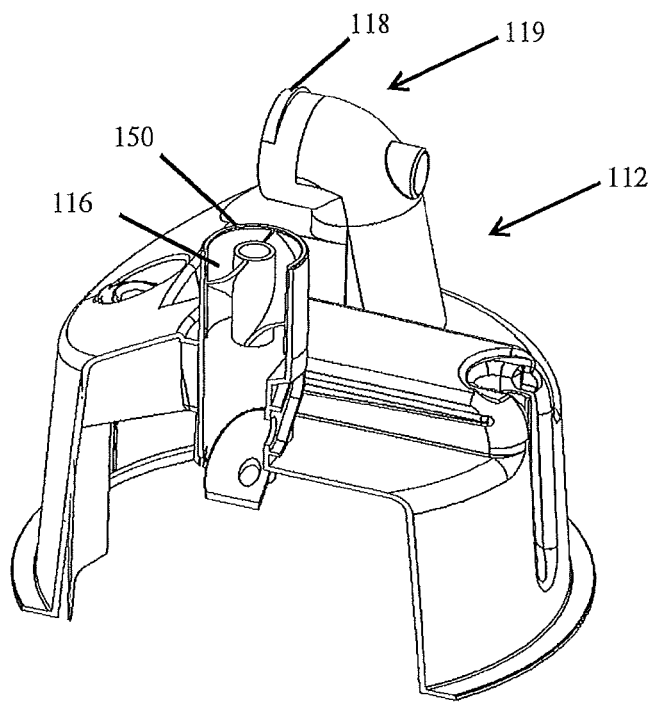
FIG. 6 shows a cross-section of a humidification chamber comprising a flow mixer, the flow mixer being similar to those described in FIGS. 5A-5G.
Figure 7:
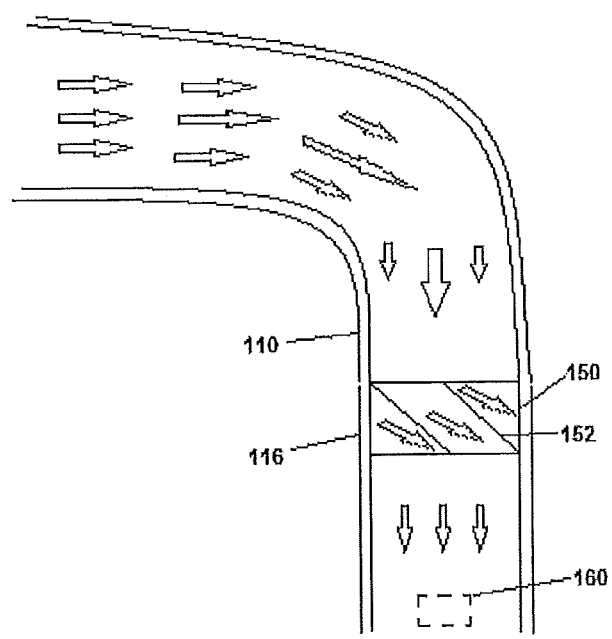
FIG. 7 shows a diagram of a section of a gases passageway of a respiratory therapy device comprising a flow mixer similar to those described in FIGS. 5A-5G or FIG. 6.
Figure 8A:
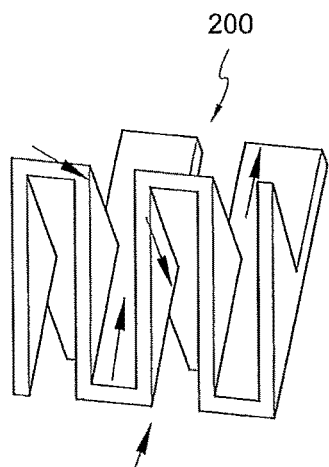
FIGS. 8A-8E show various static mixing structures.
Figure 8B:
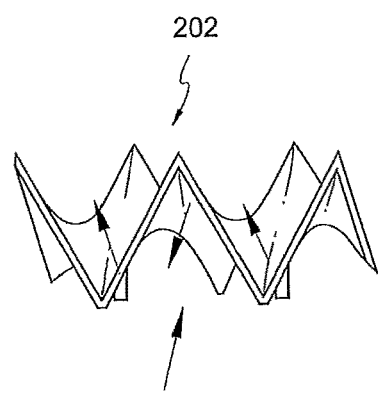
Figure 8C:
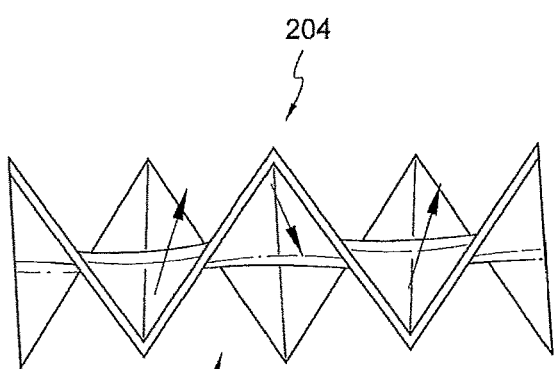
Figure 8D:
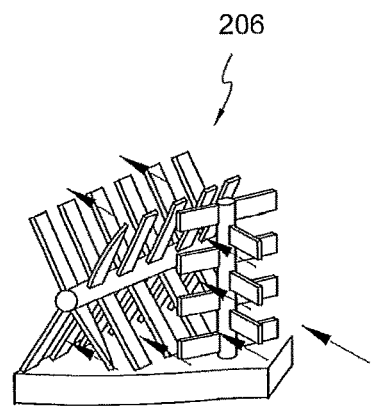
Figure 8E:
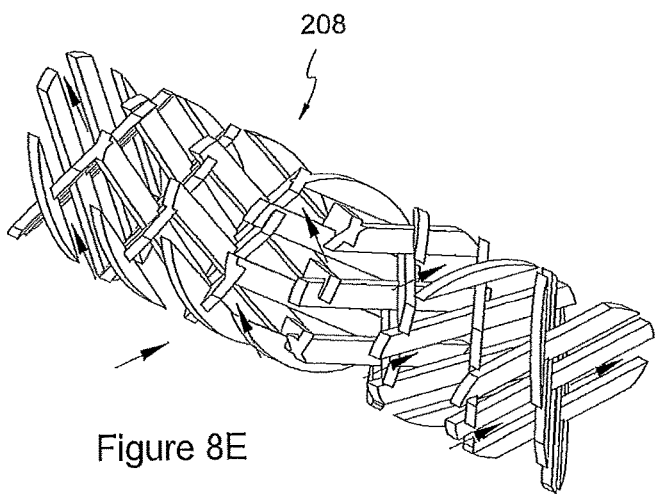

FIGS. 6 and 7 illustrate a possible use of the flow mixer 150. FIG. 6 shows that the flow mixer 150 may be located in the humidifier inlet 116 of the humidifier 112 illustrated in FIG. 2. FIG. 7 shows a diagram of a gases passageway including the humidifier inlet 116 of FIG. 6 wherein the first conduit 110 is connected to the humidifier inlet 116 as illustrated in FIG. 1. In some configurations, the conduit connector 115 (not shown in FIG. 7) may be positioned in-line between the first conduit 110 and the humidifier inlet 116 as illustrated in FIG. 3. The arrows of FIG. 7 may demonstrate the velocity of a flow of gases passing through the gases passageway in use, where the size and/or length of the arrows relates to the magnitude of the velocity of the flow of gases. As shown in FIG. 7, the velocity of a flow of gases along the bend in the first conduit 110 (or the conduit connector 115, for example) may become asymmetric along a given profile of the gases passageway.

When gases flow along the vanes 152 of the flow mixer 150 inserted in the humidifier inlet 116, the tangential motion imparted to the flow of gases may facilitate gases mixing such that the velocity of the flow of gases along the profile becomes more symmetric. This may improve the accuracy of a sensor 160 positioned in the gases passageway downstream of the flow mixer 150. The sensor 160 may be positioned in, for example, one or more of the apertures 134A, 134B, 134C as illustrated in FIG. 2. In some embodiments, configurations of flow mixing apparatus such as the conduit connector 115 illustrated in FIGS. 4A-4D may be used together with configurations of flow mixers including those illustrated in FIGS. 5A-5G. The flow mixing apparatus 115 and the flow mixer 150 may work synergistically together.

In some configurations, other static flow mixers may be used instead of or in combination with the aforementioned flow mixers and/or flow mixing apparatus, including those known as "cut and fold" and/or "twist and divide" mixers. FIGS. 8A-8E illustrate other static mixers that may advantageously be used to promote gases mixing. In each of FIGS. 8A-8E, gases may be introduced along arrows and travel along the mixers 200, 202, 204, 206, 208 shown according to the black arrows as illustrated.

FIGS. 9A-9G illustrate various views of another example embodiment of a flow mixer or flow conditioner 300. While the embodiments described above were described as being positioned upstream of a sensor, the embodiment illustrated in FIGS. 9A-9G is designed to be positioned such that the sensor is located between an inlet end and outlet end of the flow conditioner 300. In other words, the sensor can be positioned such that the sensor is disposed along the flow conditioner 300. In some configurations, however, the flow conditioner 300 of FIGS. 9A-9G can be positioned upstream, or at least a portion is positioned upstream, of at least one sensor.

In some embodiments, the humidification chamber 114 includes an elbow-shaped or angled outlet port 119 extending between the reservoir 128 and the humidifier outlet 118, for example as shown in FIGS. 2-3, 4B, 6, and 10. With reference to FIG. 10, the humidification chamber 114 can include an aperture 135A proximate to the humidifier inlet 116. The aperture 135A is configured to receive a sensor. The sensor can be, for example, a thermistor adapted to sense the temperature of gases passing through the humidifier inlet 116. The elbow-shaped outlet port 119 can include two apertures 135B, 135C. The apertures 135B, 135C can be configured to receive sensors. The sensors can be, for example, a pair of thermistors (where one of the pair of thermistors is configured to act as a reference) adapted to measure the flow rate of gases passing through the elbow-shaped outlet port 119. The apertures 135B, 135C are positioned such that they can be viewed through the open outlet end of the outlet port 119.

As shown in the sectioned view of FIG. 11, at least some of the gases passing from the body of the humidification chamber 114, into the outlet port 119, and out of the humidifier outlet 118, as indicated by a flow path 170 in FIG. 11, pass around an arcuate bend that partially defines a connection between the body of the chamber 114 and the outlet port 119, indicated by an arrow 172. When the gases pass around the bend, flow separation can occur, promoting the creation of a turbulent boundary layer 174 near the sensors received in apertures 135B, 135C. Turbulent flow at the boundary layer 174 has a varying velocity for a given average flow rate and can reduce the consistency of the sensor output at any given system flow rate. Turbulence in the gas flow can additionally increase flow resistance through the outlet port 119, which in turn increases the pressure drop, which can inhibit the ability to deliver gases to a patient at a desired pressure. Flow mixers, such as those described herein, disposed in or near the humidifier inlet 116 can help mitigate turbulence and/or can help normalize the velocity of gases passing through the humidifier inlet 116; however, it is possible to further improve the system with respect to flow through the outlet port 119.

Instead of or in addition to a flow mixer placed in or near the humidifier inlet 116, in some embodiments, a flow mixer or conditioner, such as the flow conditioner 300 shown and described herein, can be disposed in the elbow-shaped outlet port 119, for example as shown in the various views of FIGS. 14A-14J. The flow conditioner 300 is configured to help reduce or eliminate the turbulence of gas flow in the elbow-shaped outlet port 119. More particularly, the flow conditioner 300 can help reduce or eliminate the turbulence of gas flow in a region that includes the sensors. In some configurations, the flow conditioner 300 divides the flow passing through the outlet port 119. By dividing the flow passing through the outlet port 119, the flow conditioner 300 improves sensor output performance particularly when the sensor has output that is sensitive to changes in flow velocity. Thus, the flow conditioner 300 provides for improved probe precision (in other words, reduces output variability by reducing flow turbulence around the region of the probes) while also reducing or minimizing the impact of the flow conditioner 300 on pressure drop and/or flow restriction.

As shown in FIGS. 9A-9E, the flow conditioner 300 includes multiple baffles. In the illustrated configuration, the flow conditioner 300 includes four baffles 310, 312, 314, 316 that create four compartments 320, 322, 324, 326. The baffles 310, 312, 314, 316 can be configured such that a cross-section of the flow conditioner 300 has a cross or X shape. Other configurations also are possible. For example, but without limitation, in some configurations, one or more of the baffles 310, 312, 314, 316 can be omitted. In some configurations, the baffle 312 can be omitted. In some configurations, the baffle 310 can be omitted.

In some embodiments, two or more of the baffles 310, 312, 314, 316 can be integrally formed or molded with each other. In some embodiments, two or more of the baffles 310, 312, 314, 316 are formed separately and attached to one another. The flow conditioner 300 can be permanently or removably disposed in the outlet port 119 and can be coupled to the outlet port 119 via an adhesive, a friction fit, or any other suitable means. In some embodiments, the flow conditioner 300 is integrally formed with the chamber 114.

With reference to FIGS. 9F, 9G, 12 and 13, the flow conditioner 300 can include an outlet port retention feature 330 configured to help retain the flow conditioner 300 in the appropriate position within the outlet port 119. A snap-fit can be used to secure the conditioner 300 within the outlet port 119. The outlet port retention feature 330 includes a portion with a ridge or rib or the like that is adjacent to a void, gap, or opening such that the portion with the ridge or rib or the like can deflect in an elastic manner to provide a snap fit. The outlet port retention feature 330 of the embodiment of the flow conditioner 300 shown in FIGS. 9F and 9G has a different configuration from the outlet port retention feature 330 of the embodiment of the flow conditioner 300 shown in FIGS. 9A-9E. In FIGS. 9A-9E, the outlet port retention feature 330 has a void, gap or opening that is captured within the material of the flow conditioner 300, while the outlet port retention feature 330 of FIGS. 9F and 9G has a void, gap or opening that intersects with an edge of the flow conditioner 300.

Figure 12:
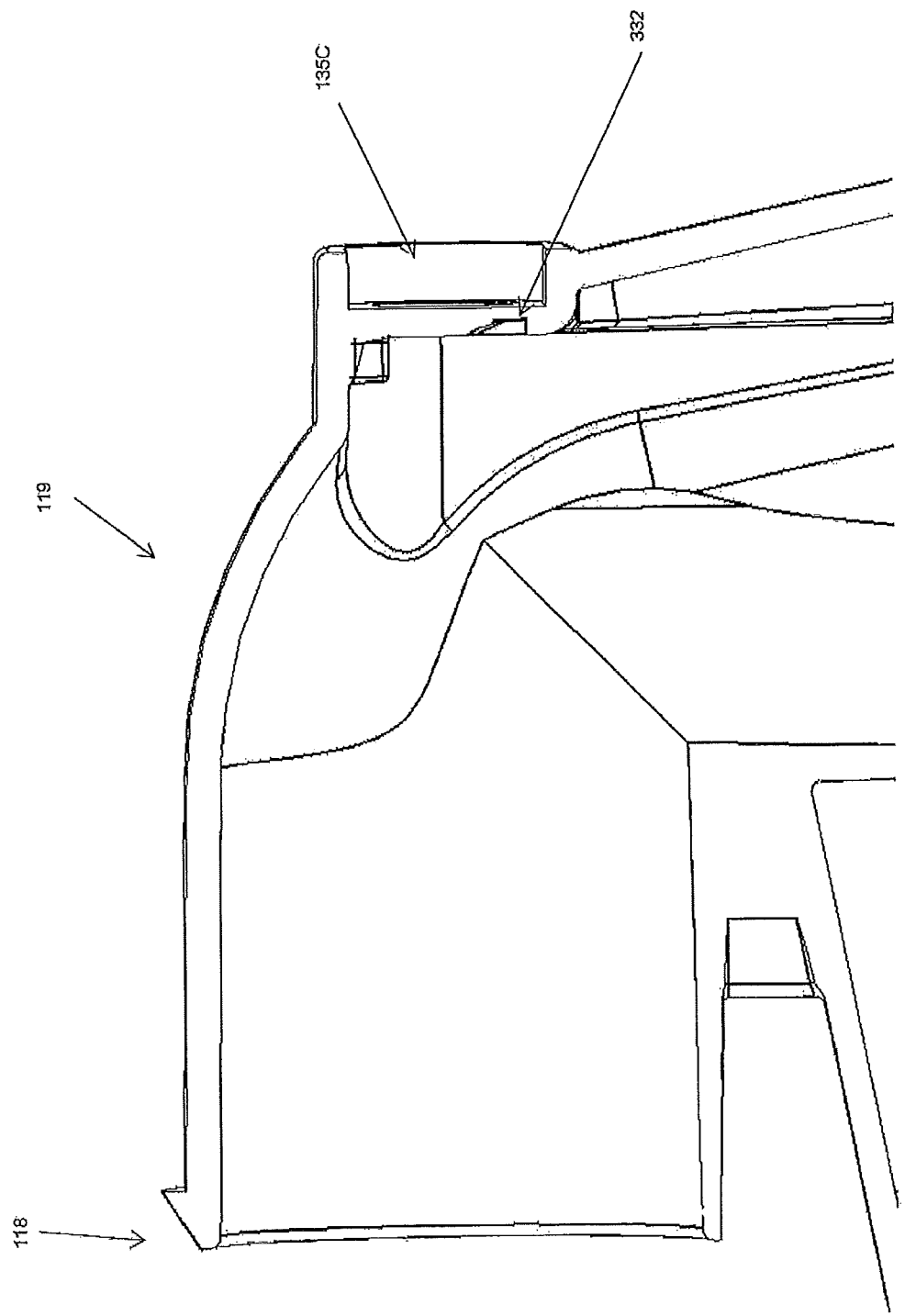
FIGS. 12 and 13 show views of the elbow-shaped outlet port and a cleft configured to receive a flow conditioner retention feature.
Figure 13:
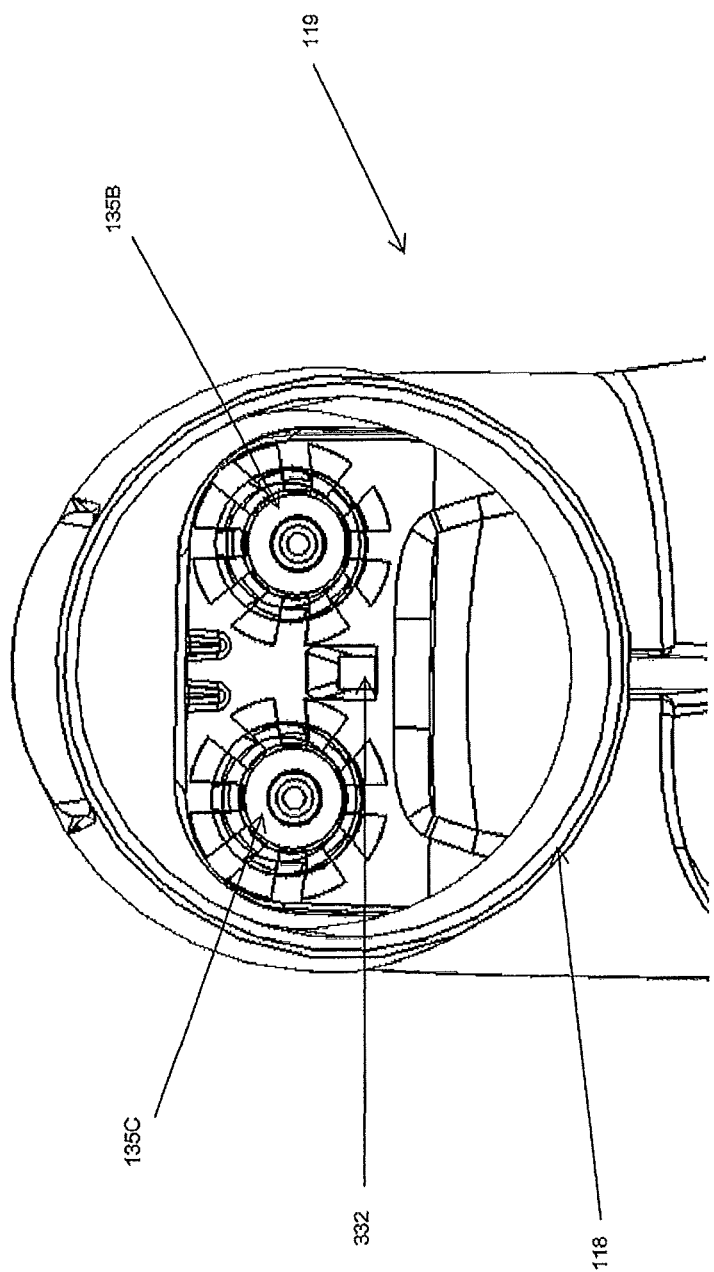
Figure 14A:
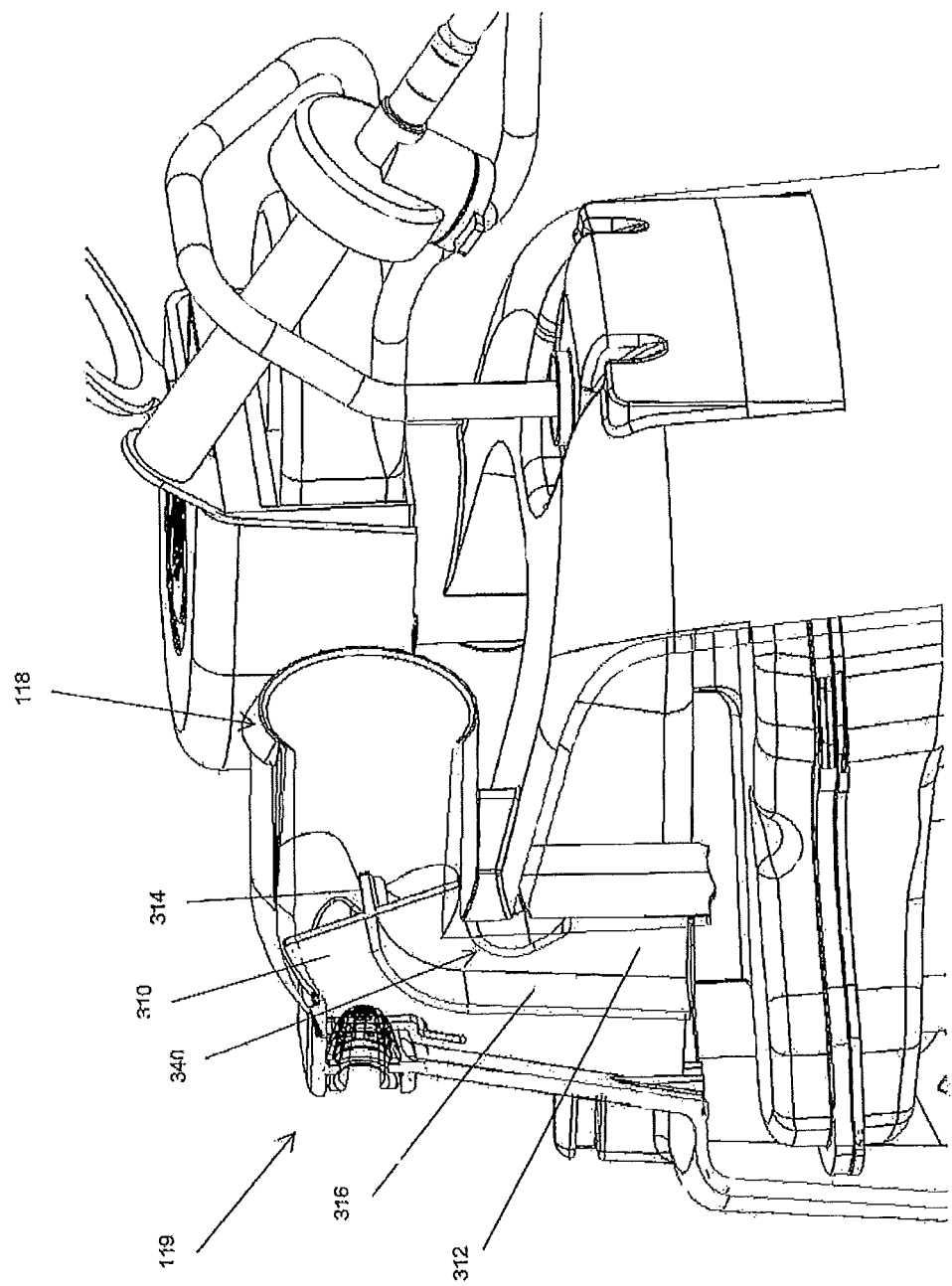
Figure 14B:
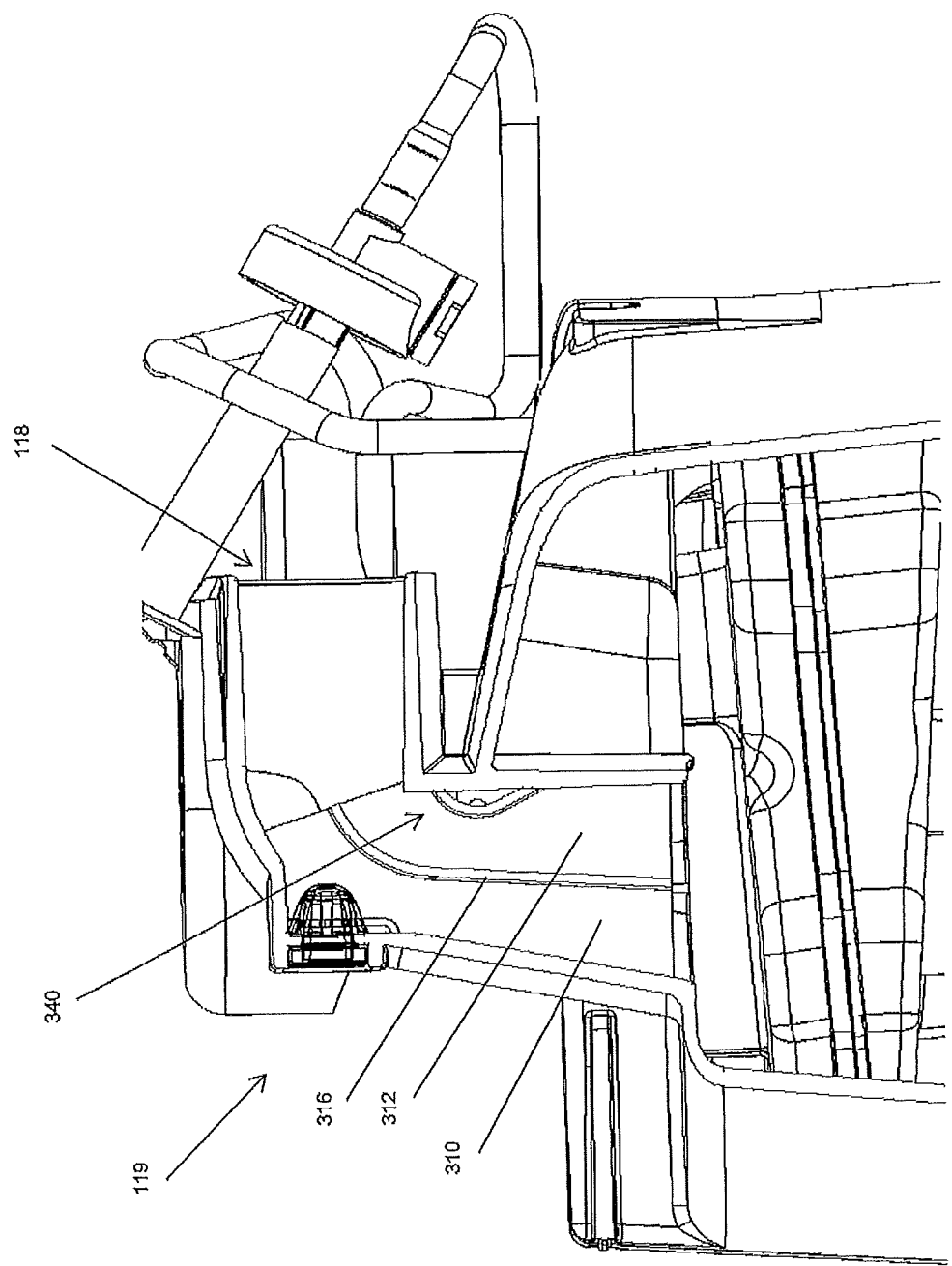
Figure 14C:
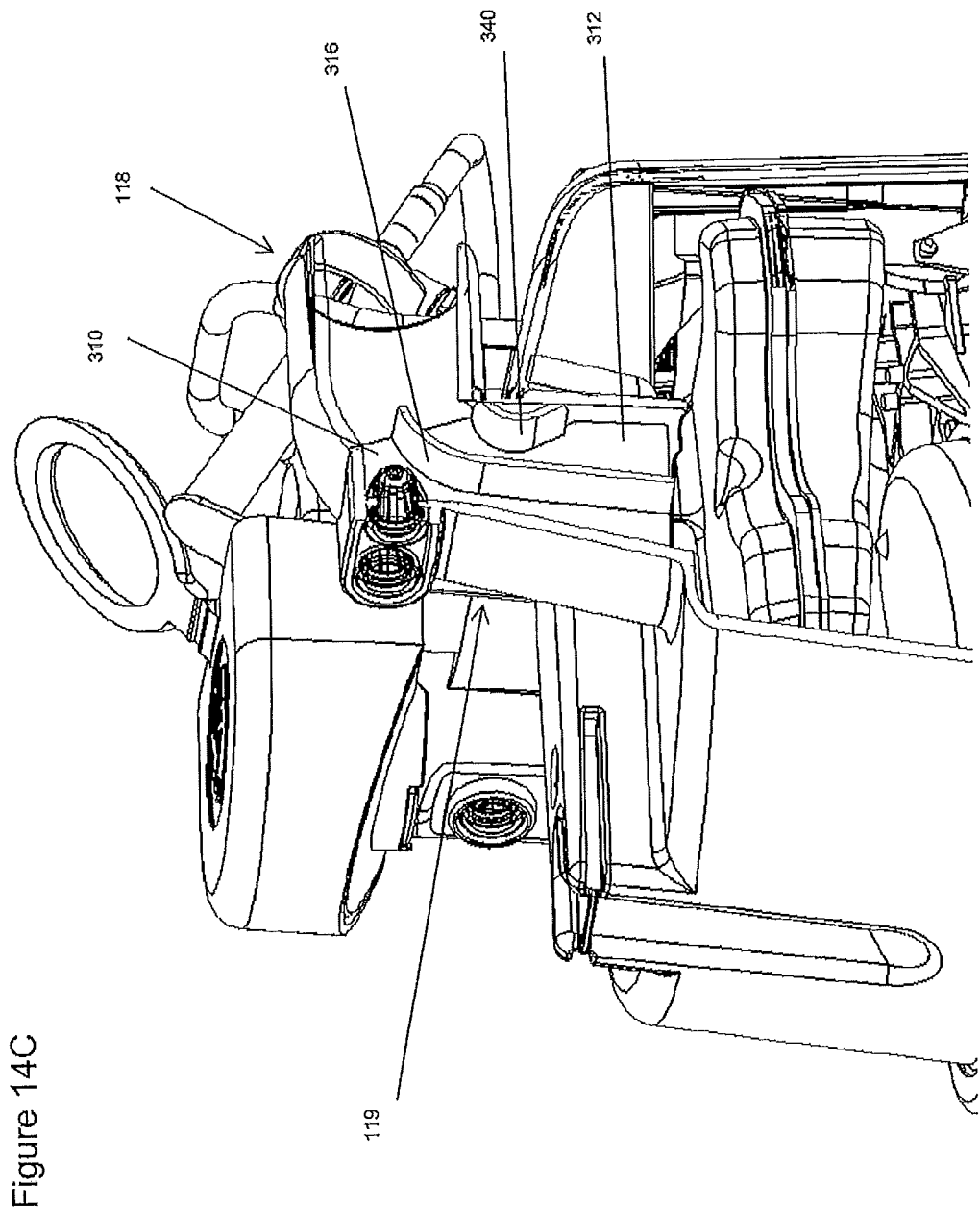
Figure 14D:
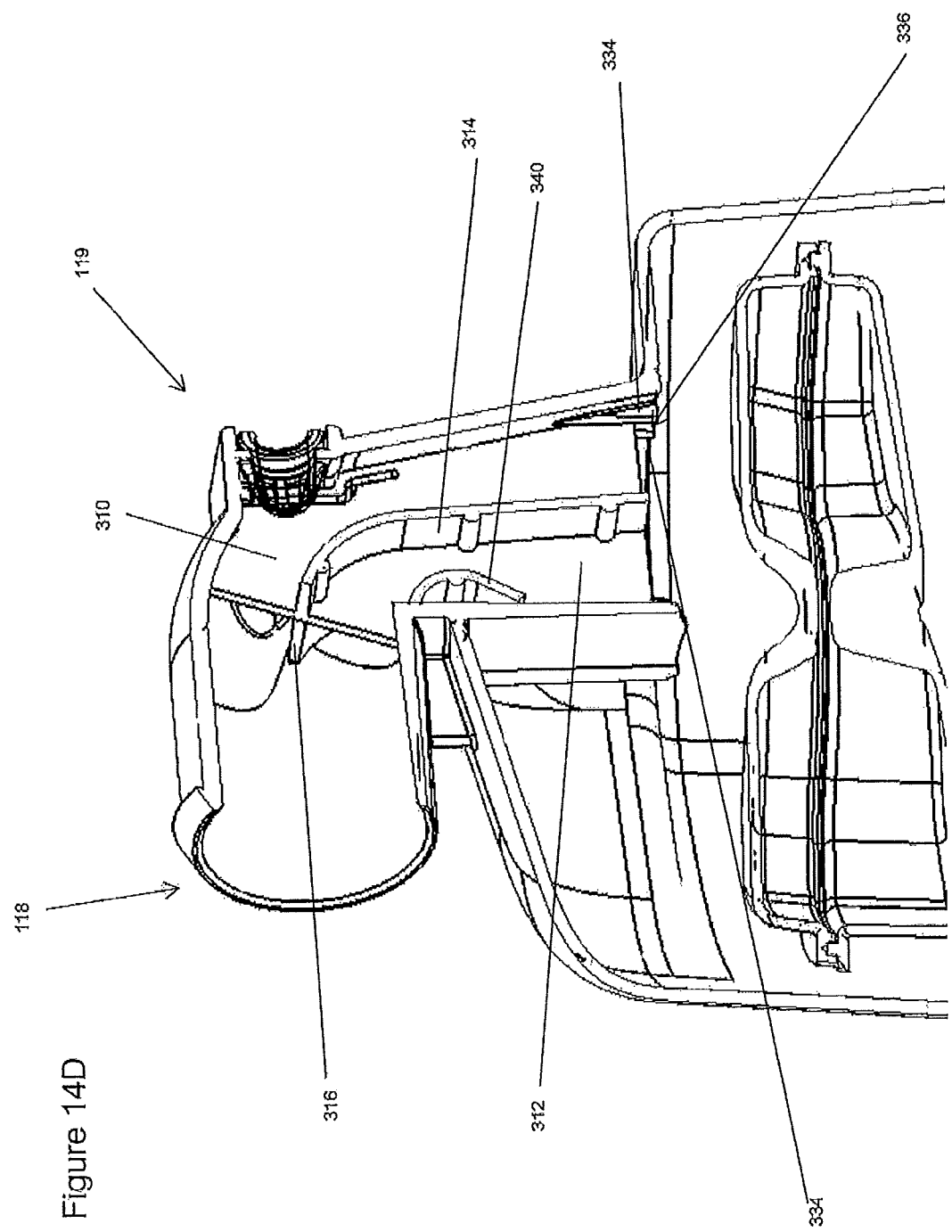
Figure 14E:
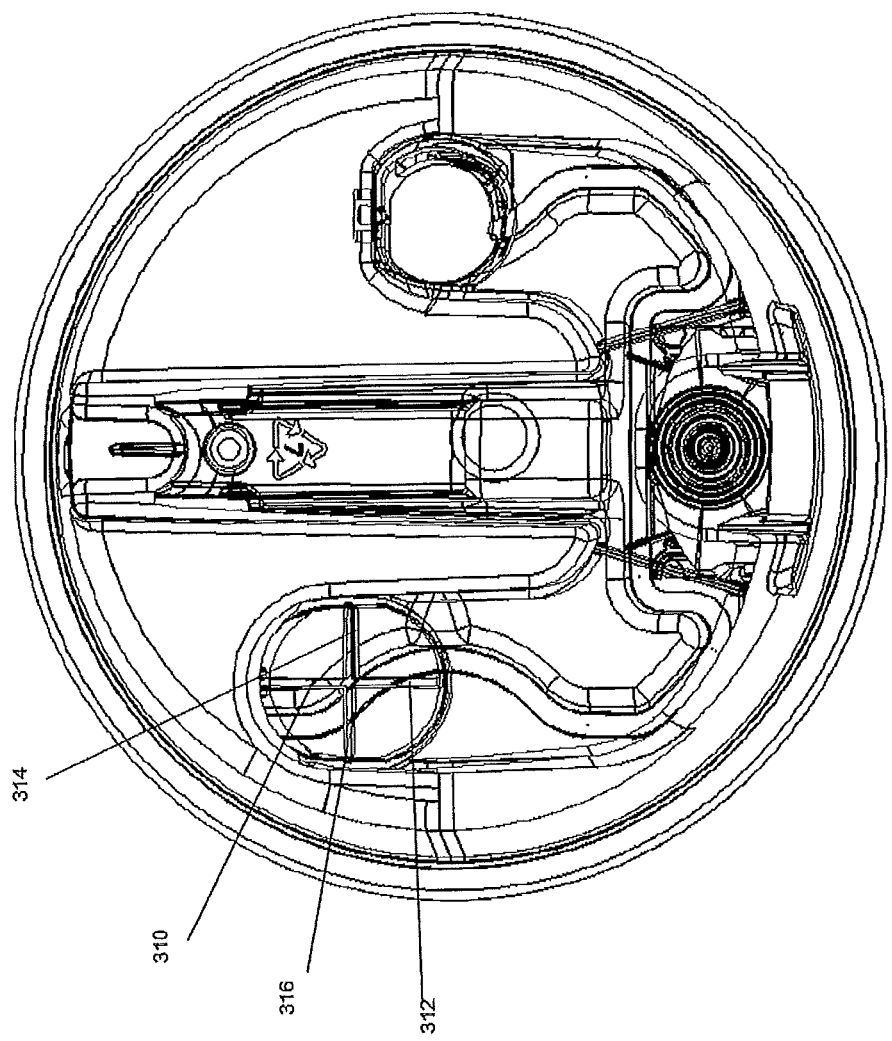
Figure 14F:
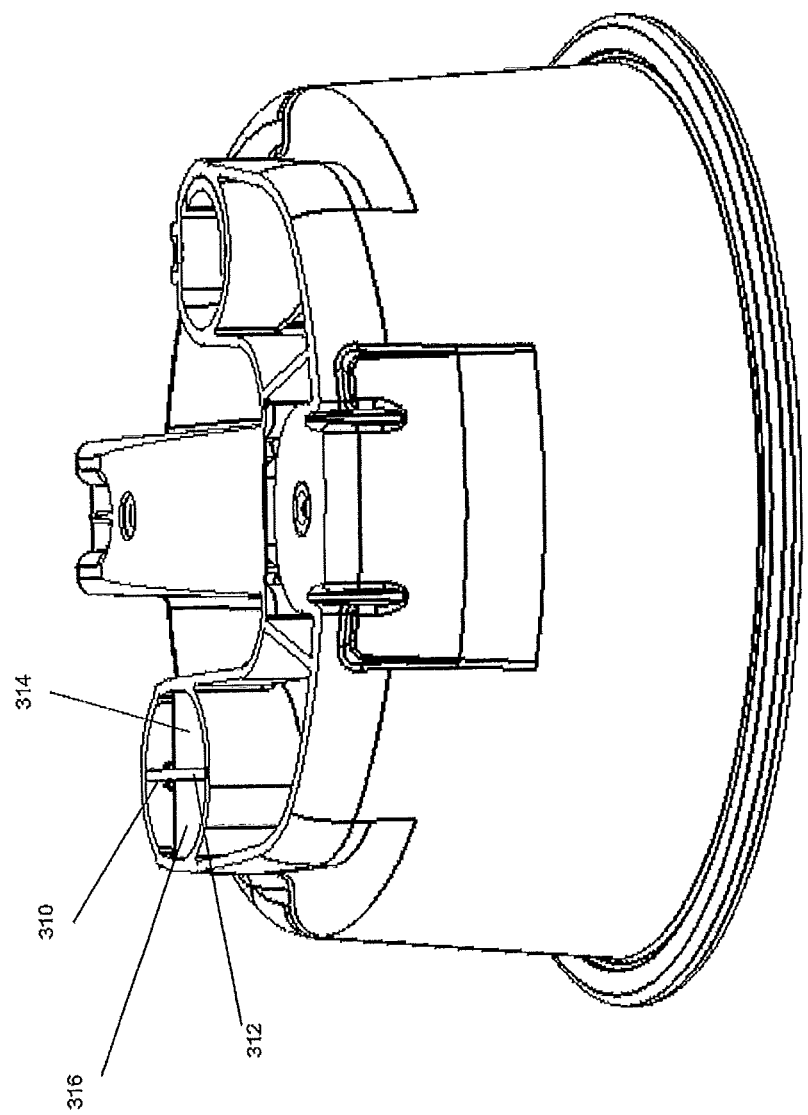
Figure 14H:
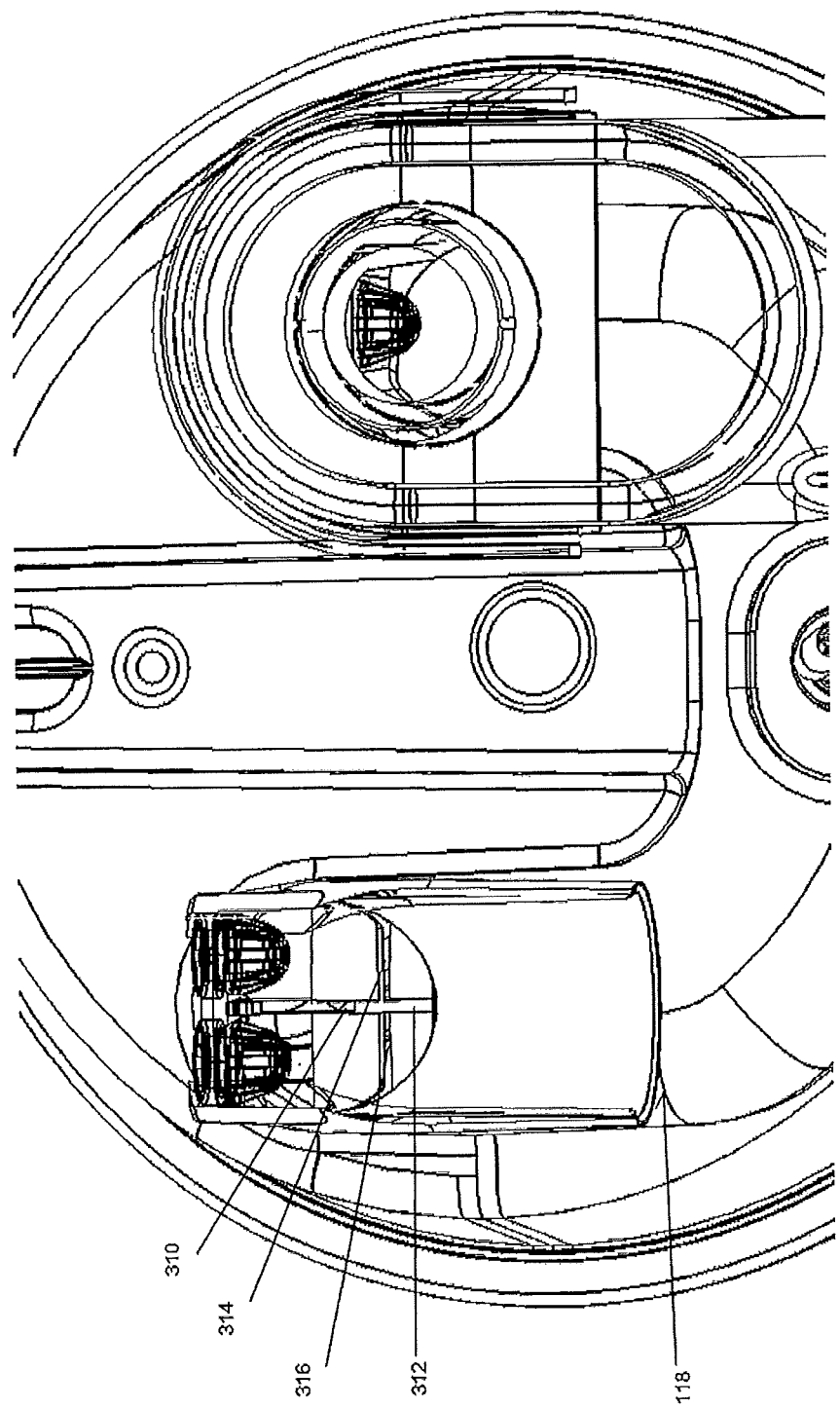
Figure 14J:
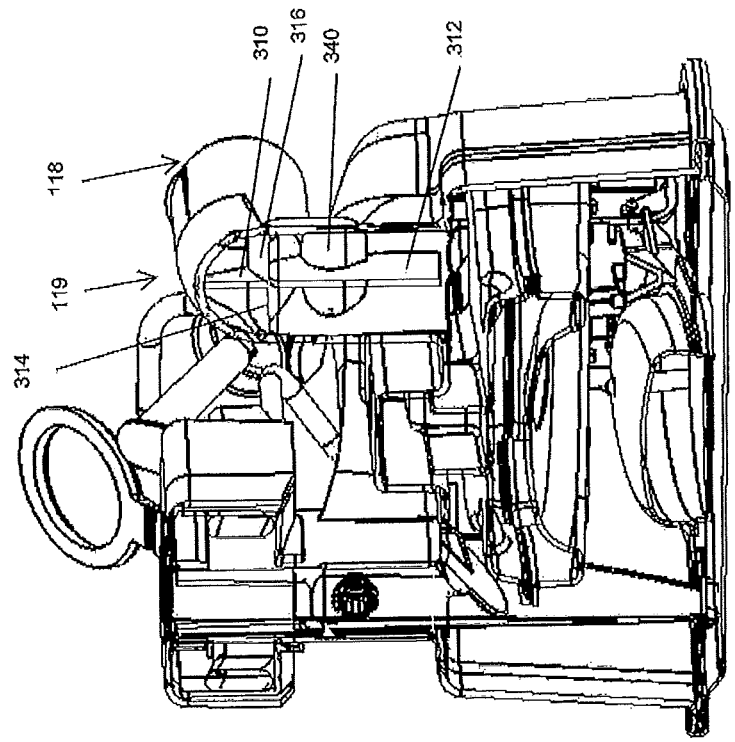
Figure 14I:
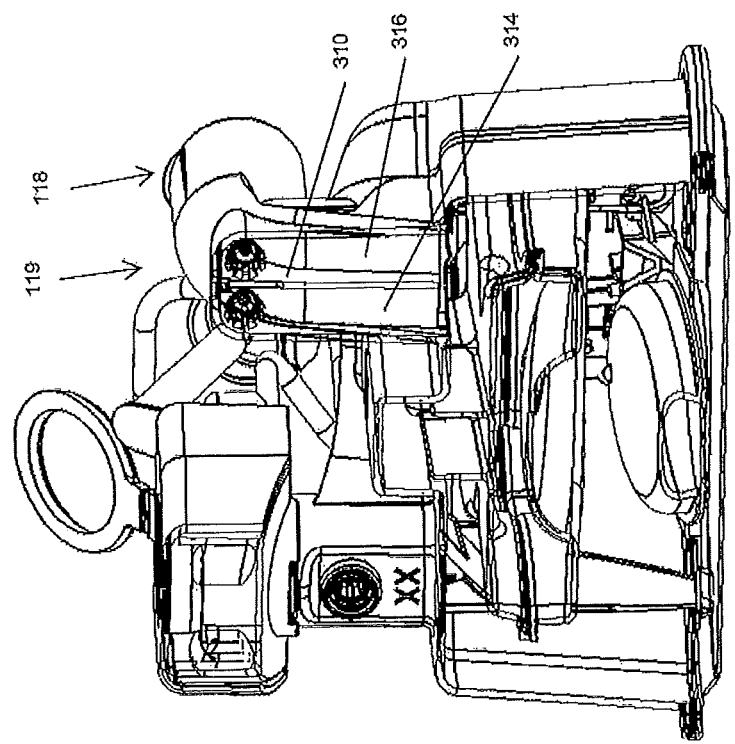
Figure 15A:
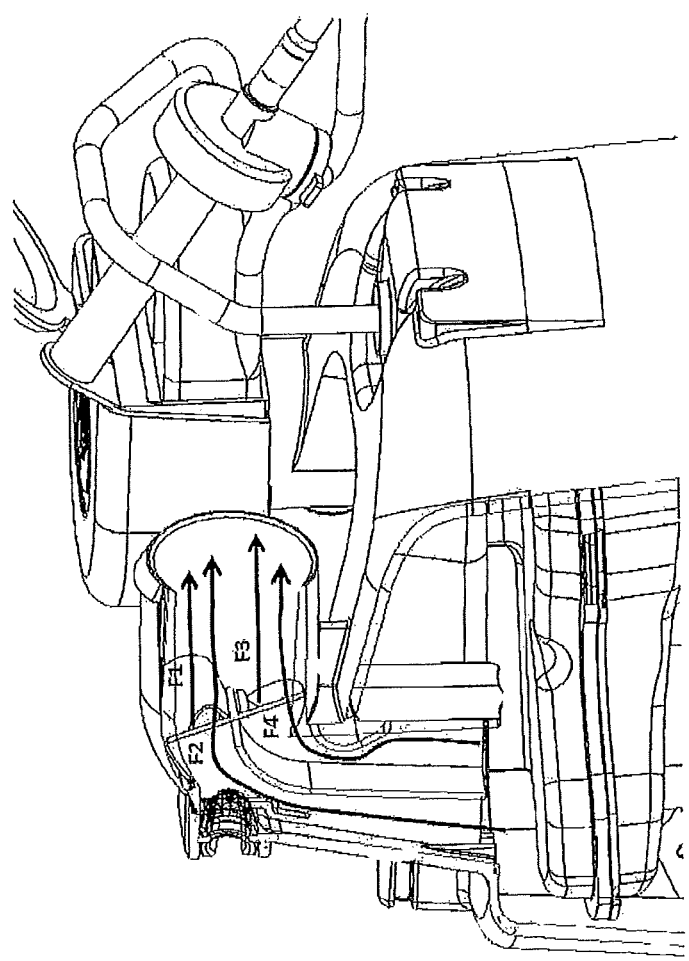
FIGS. 15A-15D show flow paths created by the flow conditioner.
Figure 15B:
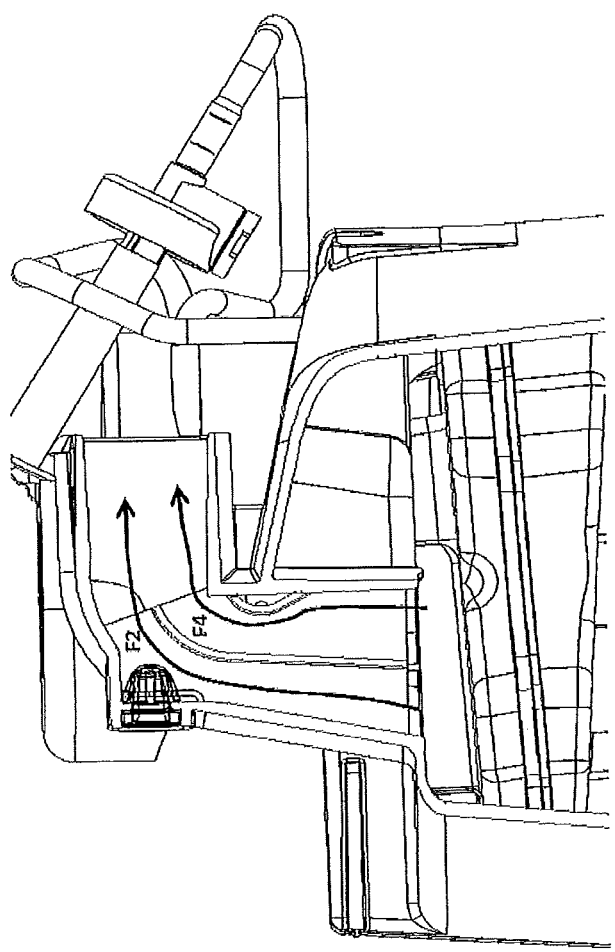
Figure 15C:
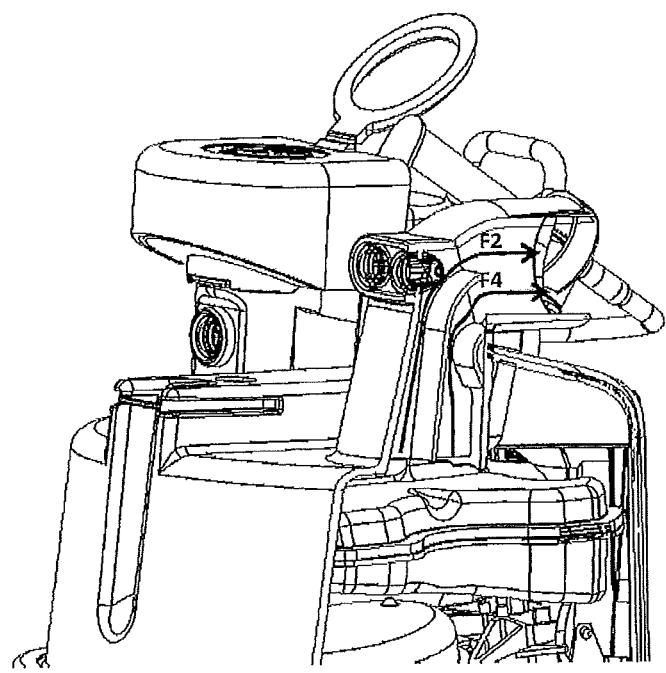
Figure 15D:
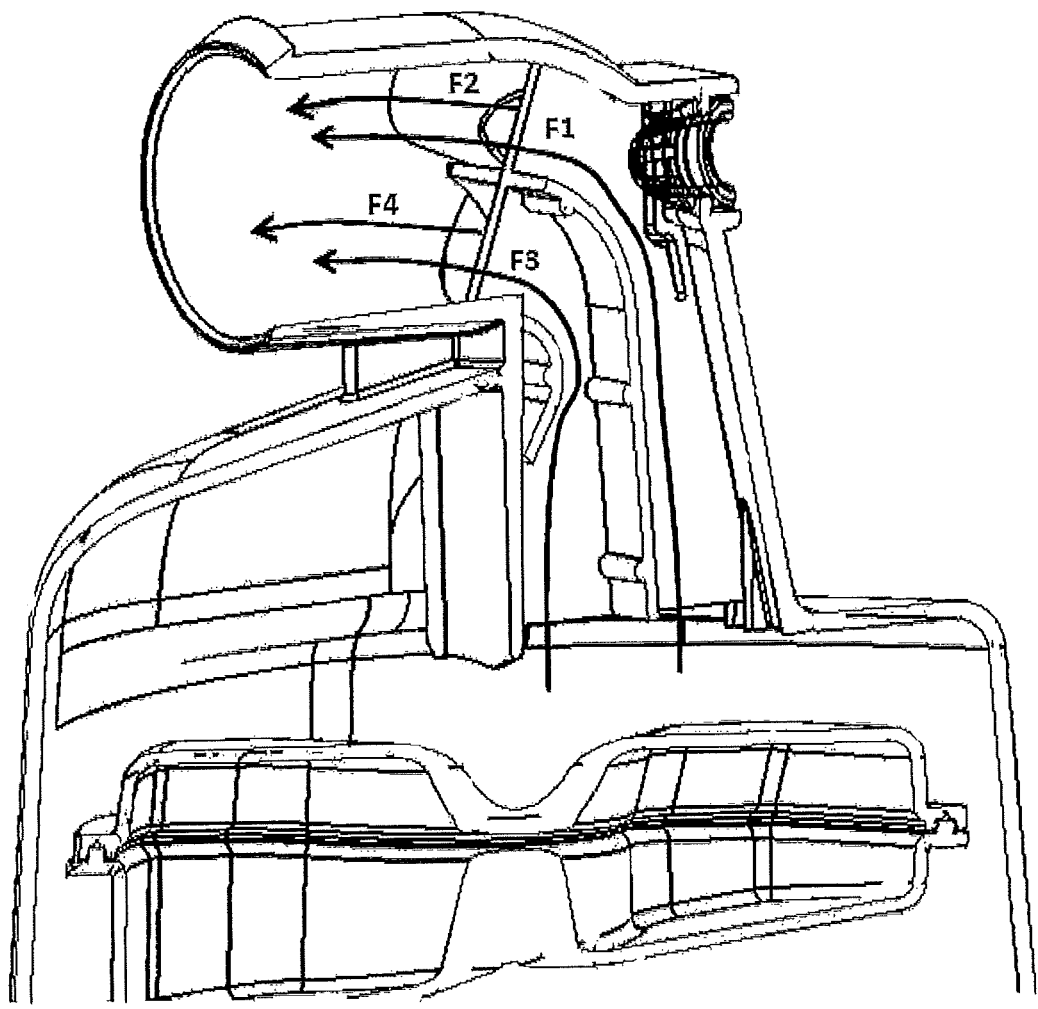

The outlet port retention feature 330 of FIGS. 9A-9G is configured to engage a corresponding cleft 332 in the wall of the outlet port 119. As shown in FIGS. 12 and 13, the cleft 332 is located proximate the apertures 135B, 135C. As shown in FIG. 14D, the outlet port 119 can include retention slats 334 at or near a base of the outlet port 119 and/or a transition between the body of the humidification chamber 114 and the outlet port 119. The slats 334 define a slot 336 configured to receive a base of the baffle 310 to orient the flow conditioner 300 during assembly and/or to help maintain the flow conditioner 300 in the appropriate position following assembly. Other configurations are possible.

Figure 9E:
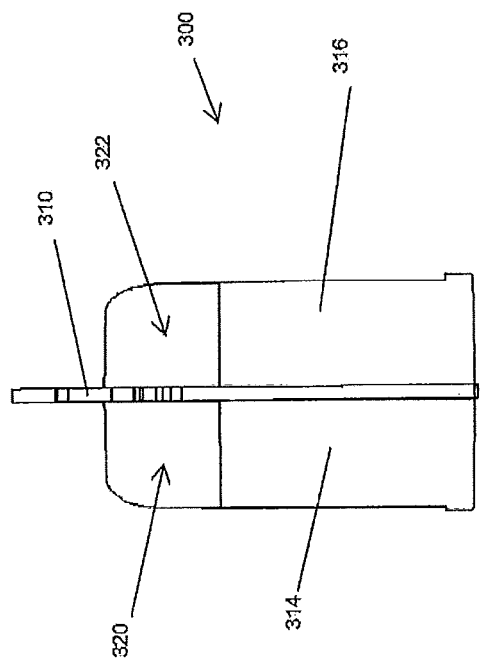
Figure 9D:
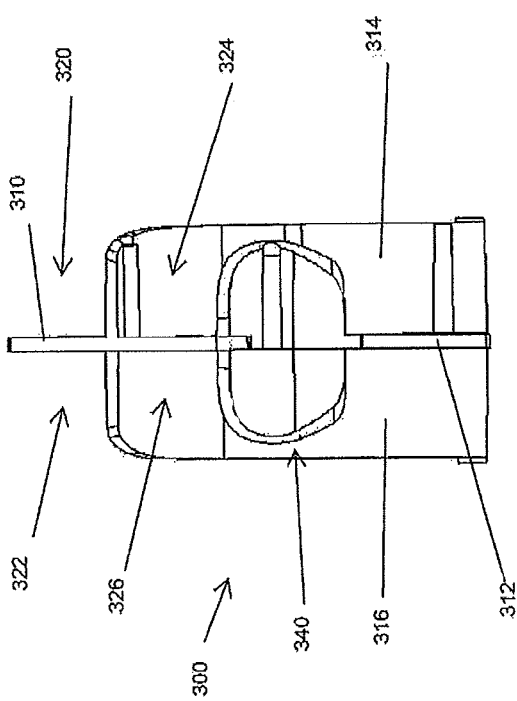
Figure 9F:
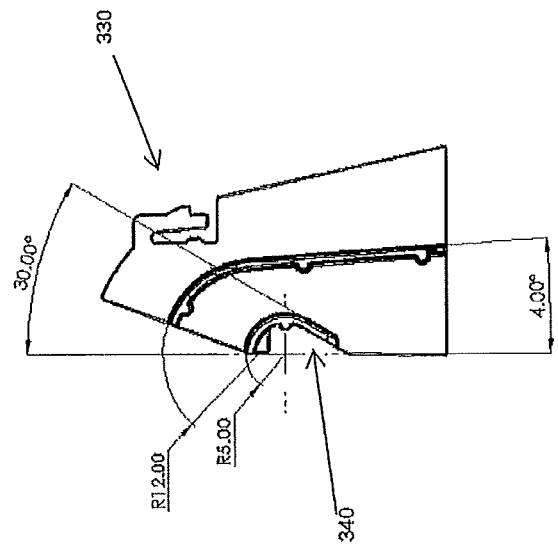
Figure 9G:
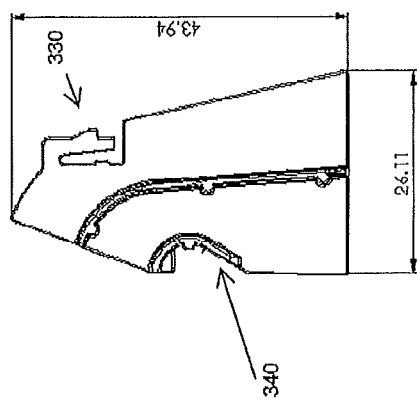

In the illustrated embodiment, the flow conditioner 300 also includes at least one aerofoil feature 340. As shown in FIG. 9D, 9F and 9G, for example, the aerofoil feature 340 is located on an edge of the baffle 312. In the illustrated configuration, the aerofoil feature 340 is located opposite of, or positioned away from, the apertures 135B, 135C when the flow conditioner 300 is disposed in the outlet port 119. The aerofoil feature 340 is separated from the apertures 135B, 135C by the baffles 314, 316. The aerofoil feature 340 can be integrally formed with or coupled to the baffle 312.

As shown, the aerofoil feature 340 is curved and convex toward the baffles 314, 316. As illustrated, the baffles 314, 316 have a straight lower portion and a curved upper portion. The illustrated baffles 314, 316 generally follow the shape or configuration of the elbow-shaped outlet port 119. In some configurations, the baffles 314, 316 define curved portions that are concentric with each other. In some embodiments, a radius of curvature of the curved upper portion of each of the baffles 314, 316 is 12 mm as shown in FIG. 9F. In some embodiments, the aerofoil feature 340 has an angled lower portion and a partially circular upper portion. The lower portion can be angled at 30° and the upper portion can have a radius of curvature of 5 mm, for example as shown in FIG. 9F. In the illustrated configuration, and as best shown in FIG. 9F and 9G, for example, the wall or walls defining the aerofoil feature 340 has at least a portion that defines a first arc while the wall or walls defining the baffles 314, 316 has at least a portion that defines a second arc. In some such configurations, the first arc and the second arc have the same center of curvature. The arcs have first ends that are coterminous with the flow conditioner 300 and second ends that connect to walls that define a tapering mouth. The first and second arcs can define a passage with a constant cross-section portion.

The flow conditioner 300 can occupy the full length of the outlet port 119 or any portion of the length of the outlet port 119. In the illustrated configuration, the flow conditioner 300 occupies only a portion of the full length of the outlet port 119. The portion of the length of the outlet port 119 occupied by the flow conditioner can contain one or more sensors or at least one or more of the apertures 135A, 135B, 135B that receive sensors. In some embodiments, a total height of the flow conditioner 300 is in the range of 43 mm to 44 mm. In some embodiments, a total width of the flow conditioner 300 is in the range of 26 mm to 27 mm.

As gases flow into the outlet port 119, the curvature of the aerofoil feature 340 allows the incoming flow to gently change in direction as it flows around a corner defined within the elbow. In the absence of the aerofoil feature 340, the gases flowing around the corner defined within the elbow are forced to turn a sharp angle. By smoothing the corner, the aerofoil feature 340 allows the flow of gases to experience less pressure drop and less increase in resistance to flow. In addition, in use, the flow conditioner 300 separates the flow of gases through the outlet port 119 into multiple (four in the illustrated embodiment) smaller compartments or flow paths.

FIGS. 15A-15D illustrate flow paths F1, F2, F3, F4 through compartments 320, 322, 324, 326, respectively, formed by the flow conditioner 300. The illustrated configuration features four compartments 320, 322, 324, 326. The smaller compartments 320, 322, 324, 326 compared to the overall size of the outlet port 119 reduce the space available for boundary layer separation and/or collision of a given portion of a flow of gases with another portion of the flow of gases, thereby helping to reduce turbulence. The gradually curved shape of the baffles 314, 316 also helps ease the flow of gases through the outlet port 119 and discourage the formation of eddies, vortices, or turbulent areas. One or more of the compartments 320, 322, 324, 326 can be configured to promote substantially laminar flow through the compartment. In some configurations, the one or more of the compartments 320, 322, 324, 326 containing sensors can be configured to promote substantially laminar flow at least in the region near the sensors. For example, removing or reducing the number and/or severity or sharp angles in or directly adjacent to the compartment can promote substantially laminar flow.

Variations of the flow conditioner 300 can include more or fewer baffles to create more or fewer compartments. Increasing the number of compartments and/or decreasing the cross-section of compartments proximal to the sensors reduces turbulence and increases sensor precision. However, increasing the number of compartments and/or decreasing the cross-section of the compartments can also increase flow restriction and pressure drop. The number of baffles and compartments should therefore be selected to balance turbulence reduction and minimization of pressure drop. In some embodiments, part or all of the baffle 312 can be eliminated to improve flow resistance. For example, the portion of the baffle 312 supporting the aerofoil feature 340, described in greater detail herein, can be maintained, and the remainder of the baffle 312 can be removed. In some embodiments, turbulation features (for example, small pits, bumps, or the like) can be placed along the curved portions of the flow conditioner 300 and/or portions of the humidification chamber 114 proximate to the base of the outlet port 119 to help discourage the formation of turbulent flow layers and thereby improve sensor precision.

Figure 16:
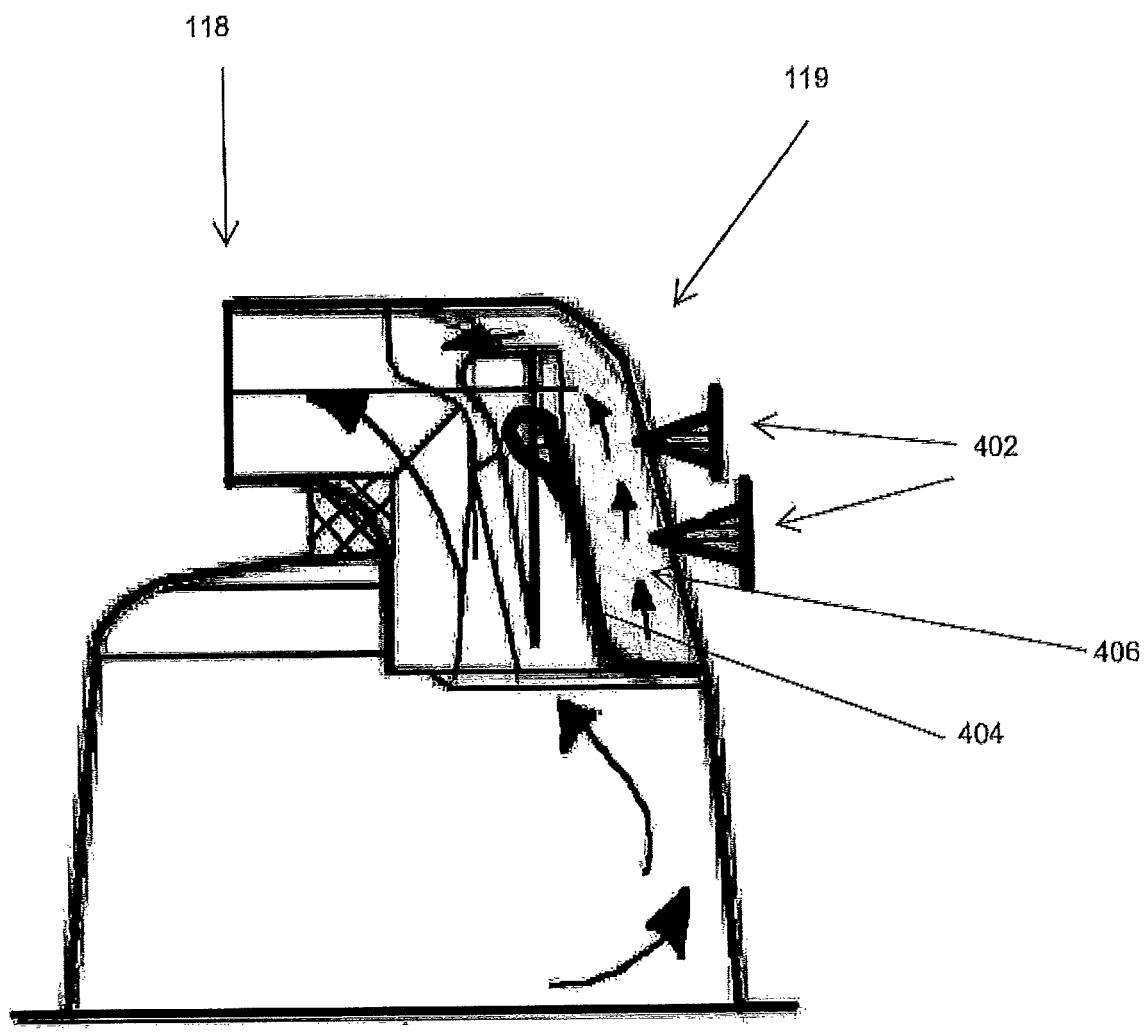
FIG. 16 shows an alternative embodiment of a flow conditioning elbow-shaped outlet port.

FIG. 16 illustrates another embodiment of the elbow-shaped outlet port 119 that includes a compartment that is configured to contain one or more sensors 402. In the illustrated configuration, the compartment can be defined by a barrier 404, such as a wall or the like. The illustrated barrier 404 is configured to create a bleed flow adjacent the sensors 402. In other words, the barrier 404 creates a discrete chamber 406 of conditioned gases flow that passes by the sensors 402 to thereby improve sensor reading accuracy. The chamber 406 can be configured to promote laminar flow in the vicinity of the sensors 402.

Unless the context clearly requires otherwise, throughout the description and the claims, the words "comprise", "comprising", and the like are to be construed in an inclusive sense as opposed to an exclusive or exhaustive sense, that is to say, in the sense of "including, but not limited to".

Where in the foregoing description reference has been made to integers or components having known equivalents thereof, those integers or components are herein incorporated as if individually set forth.

The disclosed methods, apparatus, and systems may also be said broadly to comprise the parts, elements, and features referred to or indicated in the disclosure, individually or collectively, in any or all combinations of two or more of said parts, elements, or features.

Recitation of ranges herein is merely intended to serve as a shorthand method of referring individually to each separate sub-range or value falling within the range, unless otherwise indicated herein, and each such separate sub-range or value is incorporated into the specification as if it were individually recited herein.

Reference to any prior art in this specification is not, and should not be taken as, an acknowledgement or any form of suggestion that said prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A humidification chamber for a respiratory therapy apparatus, the humidification chamber comprising:
   a body comprising a base plate, the base plate at least partially defining a reservoir;
   an inlet port extending from the body and defining a gases inlet into the body;
   an outlet port extending from the body and defining a gases outlet out of the body, the outlet port configured to receive a sensor and the outlet port configured to interface with a conduit, the outlet port having a wall defining a bent flow path through the outlet port; and
   a flow conditioner positioned within the outlet port, the flow conditioner comprising at least one internal wall, the at least one internal wall subdividing the bent flow path of the outlet port into a plurality of compartments that separate the bent flow path such that each compartment receives only a portion of an entire gas flow, wherein the sensor extends into the bent flow path and at least partially into one of the plurality of compartments.

2. The humidification chamber of claim 1, wherein the plurality of compartments are configured to promote laminar flow through at least one of the plurality of compartments into which the sensor extends at least partially.

3. The humidification chamber of claim 1, wherein the outlet port is an elbow-shaped port.

4. The humidification chamber of claim 1, wherein the at least one internal wall comprises a pair of walls.

5. The humidification chamber of claim 1, wherein the flow conditioner is removable from the outlet port.

6. The humidification chamber of claim 5, wherein the flow conditioner is configured to interface with the wall.

7. The humidification chamber of claim 5, wherein the flow conditioner comprises a deflectable elastic rib which is configured to snap fit into a gap in a wall defining at least a portion of the outlet port.

8. The humidification chamber of claim 1, wherein the plurality of compartments consist of four compartments.

9. The humidification chamber of claim 8, wherein the flow conditioner comprises four baffles that at least partially define the four compartments.

10. The humidification chamber of claim 1, the inlet port comprising a sensor port configured to receive a sensor.

11. The humidification chamber of claim 1, the outlet port comprising two sensor ports, each configured to receive a sensor.

12. The humidification chamber of claim 1, wherein the bent flow path of the outlet port defines an arcuate gas flow path out of the body of the humidification chamber.

13. The humidification chamber of claim 1, wherein at least a portion of a wall defining the bent flow path of the outlet port is angled.

14. The humidification chamber of claim 1, wherein the wall extends from the body to an outlet opening of the outlet port and the wall is tapered inwardly toward the outlet opening such that the outlet port is widest adjacent the body.

15. The humidification chamber of claim 14, wherein the outlet port comprises at least one sensor port configured to receive the sensor, the at least one sensor port positioned in an angled portion of the wall defining the outlet port.

16. The humidification chamber of claim 1, wherein the flow conditioner comprises at least one convex and curved aerofoil feature configured to smooth gas flow along the flow conditioner.

17. The humidification chamber of claim 16, wherein the outlet port comprises at least one sensor port configured to receive the sensor and the aerofoil feature is spaced from the at least one sensor port.

18. The humidification chamber of claim 1, wherein the flow conditioner comprises a curved baffle.

19. The humidification chamber of claim 1, wherein the sensor measures flow rate and temperature.

20. The humidification chamber of claim 1, wherein the sensor comprises a thermistor.

21. The humidification chamber of claim 1, the outlet port comprising a sensor port configured to receive a sensor.

22. The humidification chamber of claim 21, wherein the inlet to the flow conditioner is not axially aligned with the outlet of the flow conditioner and the flow conditioner is positioned within an elbow of the outlet port.

23. The humidification chamber of claim 22, wherein the sensor extends into the flow conditioner through the sensor port.

24. The humidification chamber of claim 23, wherein an inlet to the flow conditioner is not axially aligned with an outlet of the flow conditioner and the flow conditioner is positioned within an elbow of the outlet port.

25. The humidification chamber of claim 1, wherein the sensor extends into only one of the plurality of compartments defined by the at least one internal wall.

26. The humidification chamber of claim 1, wherein the sensor port is positioned between an inlet to the flow conditioner and an outlet from the flow conditioner.

27. The humidification chamber of claim 1, wherein the at least one internal wall is non-linear.

28. The humidification chamber of claim 1, wherein the flow conditioner is configured to minimize pressure drop caused by the flow conditioner.

* * * * *

UNITED STATES PATENT AND TRADEMARK OFFICE
CERTIFICATE OF CORRECTION

PATENT NO. : 11,324,911 B2
APPLICATION NO. : 15/315669
DATED : May 10, 2022
INVENTOR(S) : Osborne et al.

It is certified that error appears in the above-identified patent and that said Letters Patent is hereby corrected as shown below:

In the Specification

In Column 1, Line 63, delete "bend," and insert --bend.--.

In Column 2, Line 51, delete "pitch," and insert --pitch.--.

In Column 2, Line 58, delete "system," and insert --system.--.

In Column 4, Line 20, delete "FIG. 3," and insert --FIG. 3.--.

In Column 4, Lines 25-26, delete "mixers," and insert --mixers.--.

In Column 4, Line 55, delete "100," and insert --100.--.

In Column 7, Line 52, delete "131" and insert --133.--.

In Column 8, Line 22, delete "FIG. 2" and insert --FIG. 2.--.

In the Claims

In Column 17, Claim 22, should read --The humidification chamber of Claim 21, wherein the sensor port is positioned between an inlet to the flow conditioner and an outlet from the flow conditioner.--.

In Column 18, Claim 24, Line 4, delete "an" and insert --the--.

In Column 18, Claim 24, Line 5, delete "an" and insert --the--.

In Column 18, Claim 26, should read --The humidification chamber of Claim 21, wherein an inlet to the flow conditioner is not axially aligned with an outlet of the flow conditioner and the flow conditioner is positioned within an elbow of the outlet port.--.

Signed and Sealed this
Eighteenth Day of October, 2022

Katherine Kelly Vidal
*Director of the United States Patent and Trademark Office*